(12) United States Patent
Pulé et al.

(10) Patent No.: US 10,478,457 B2
(45) Date of Patent: Nov. 19, 2019

(54) CHIMERIC PROTEIN

(71) Applicant: UCL BUSINESS PLC, London (GB)

(72) Inventors: Martin Pulé, London (GB); Ryan Trowbridge, London (GB); Edward Hodgkin, London (GB)

(73) Assignee: UCL BUSINESS LTD, London (GB)

( * ) Notice: Subject to any disclaimer, the term of this patent is extended or adjusted under 35 U.S.C. 154(b) by 0 days.

(21) Appl. No.: 16/113,098

(22) Filed: Aug. 27, 2018

(65) Prior Publication Data

US 2019/0015451 A1  Jan. 17, 2019

Related U.S. Application Data

(63) Continuation of application No. 15/526,097, filed as application No. PCT/GB2016/050451 on Feb. 23, 2016, now Pat. No. 10,098,911.

(30) Foreign Application Priority Data

Feb. 24, 2015  (GB) .................................. 1503133.9

(51) Int. Cl.
| | | |
|---|---|---|
| *A61K 35/17* | (2015.01) | |
| *C12N 9/64* | (2006.01) | |
| *A61K 31/436* | (2006.01) | |
| *C12N 15/62* | (2006.01) | |
| *C07K 14/705* | (2006.01) | |
| *C12N 9/12* | (2006.01) | |
| *A61K 35/12* | (2015.01) | |

(52) U.S. Cl.
CPC ............ *A61K 35/17* (2013.01); *A61K 31/436* (2013.01); *C07K 14/705* (2013.01); *C12N 9/1205* (2013.01); *C12N 9/6472* (2013.01); *C12N 15/62* (2013.01); *C12Y 304/22062* (2013.01); *A61K 2035/124* (2013.01); *C07K 2319/70* (2013.01); *Y02A 50/411* (2018.01)

(58) Field of Classification Search
CPC .............................. A61K 35/17; C12N 9/6472
See application file for complete search history.

(56) References Cited

U.S. PATENT DOCUMENTS

| | | |
|---|---|---|
| 6,916,917 B1 | 7/2005 | Baltimore et al. |
| 2002/0107189 A1 | 8/2002 | Clackson et al. |
| 2004/0040047 A1 | 2/2004 | Spencer et al. |
| 2016/0166613 A1* | 6/2016 | Spencer ................ A61K 35/17 424/93.21 |
| 2016/0311917 A1 | 10/2016 | Beatty et al. |

FOREIGN PATENT DOCUMENTS

| | | |
|---|---|---|
| WO | WO-1996/041865 A1 | 12/1996 |
| WO | WO-1999/050425 A2 | 10/1999 |
| WO | WO-2003/089627 A1 | 10/2003 |
| WO | WO-2012/177927 A1 | 12/2012 |
| WO | WO-2014/127261 A1 | 8/2014 |
| WO | WO-2014/197638 A2 | 12/2014 |
| WO | WO-2015/090230 A1 | 6/2015 |
| WO | WO-2015/134877 A1 | 9/2015 |
| WO | WO-2015/150771 A1 | 10/2015 |
| WO | WO-2016/100241 A2 | 6/2016 |

OTHER PUBLICATIONS

Amara et al., Cell surface tagging and a suicide mechanism in a single chimeric human protein, *Hum. Gene Ther.* 10:2651-5 (1999).
Bayle et al., Rapamycin analogs with differential binding specificity permit orthogonal control of protein activity, *Chem. Biol.* 13:99-107 (2006).
Di Stasi et al., Inducible apoptosis as a safety switch for adoptive cell therapy, *N. Engl. J. Med.* 365:1673-83 (2011).
Fegan et al., Chemically controlled protein assembly: techniques and applications, *Chem. Rev.* 110:3315-36 (2010).
International Search Report and Written Opinion, International Application No. PCT/GB2016/050451, dated May 2, 2016.
Introna et al., Genetic modification of human T cells with CD20: a strategy to purify and lyse transduced cells with anti-CD20 antibodies, *Hum. Gene Ther.* 11:611-20 (2000).
Iuliucci et al., Intravenous safety and pharmacokinetics of a novel dimerizer drug, AP1903, in healthy volunteers, *J. Clin. Pharmacol.* 41:870-9 (2001).
Kieback et al., A safeguard eliminates T cell receptor gene-modified autoreactive T cells after adoptive transfer, *Proc. Natl. Acad. Sci. USA.* 105:623-8 (2008).
Lupas et al., The Structure of α-Helical Coiled Coils, Adv. *Protein Chem.* 70:37-38 (2005).
Morgan et al., Turning on caspases with genetics and small molecules, *Methods Enzymol.* 544:179-213 (2014).
Philip et al., A highly compact epitope-based marker/suicide gene for easier and safer T-cell therapy, *Blood.* 124:1277-87 (2014).
Straathof et al., An inducible caspase 9 safety switch for T-cell therapy, *Blood.* 105:4247-54 (2005).
Third Party Observation filed in counterpart application EP20160707195.
Wang et al., A transgene-encoded cell surface polypeptide for selection, in vivo tracking, and ablation of engineered cells, *Blood.* 118:1255-63 (2011).
Binkowski et al., "Ligand-Regulated Peptides: A General Approach for Modulating Protein-Peptide Interactions with Small Molecules," Chemistry & Biology 12:847-855 (2005).

(Continued)

*Primary Examiner* — Scott Long
(74) *Attorney, Agent, or Firm* — Marshall, Gerstein & Borun LLP

(57) ABSTRACT

The present invention provides a chimeric protein having the formula: Casp-Ht1-Ht2 wherein Casp is a caspase domain; Ht1 is a first heterodimerization domain; and Ht2 is a second heterodimerization domain and wherein, in the presence of a chemical inducer of dimerization (CID), an identical pair of the chimeric proteins interact such that Ht1 from one chimeric protein heterodimerizes with Ht2 from the other chimeric protein, causing homodimerization of the two caspase domains. The invention also provides a cell comprising such a protein and its use in adoptive cell therapy.

13 Claims, 14 Drawing Sheets
Specification includes a Sequence Listing.

(56) References Cited

OTHER PUBLICATIONS

Gray et al., "Activation of Specific Apoptotic Caspases with an Engineered Small-Molecule-Activated Protease," Cell 142:637-646 (2010).
Li et al., "A novel conditional Akt 'survival switch' reversibly protects cells from apoptosis," Gene Therapy 9:233-244 (2002).
Mace et al., "Caspae Enzymology and Activation Mechanisms," Methods Enzymolo. 544:161-78 (2014).
Xu et al., "Conditionally controlling nuclear trafficking in yeast by chemical-induced protein dimerization," Nature Protocols 5(11):1831-1843 (2010).

* cited by examiner

CHIMERIC PROTEIN

FIELD OF THE INVENTION

The present invention relates to a chimeric protein useful in adoptive cell therapy (ACT). The chimeric protein can act as a suicide gene enabling cells expressing the chimeric protein to be deleted. The present invention also provides a nucleic acid encoding such a chimeric protein, a cell comprising such a nucleic acid and therapeutic uses thereof.

BACKGROUND TO THE INVENTION

Adoptive Cell Therapy

Adoptive immunotherapy is an established and evolving therapeutic approach. In the setting of allogeneic haematopoietic stem cell transplantation (HSCT), donor lymphocyte infusions (DLI) are frequently given to treat relapse of haematological malignancies. Tumour infiltrating lymphocytes (TILs) are effective in treating metastatic melanoma. Genetic engineering of T-cells greatly increases the scope and potency of T-cell therapy: T-cell receptor transfer allows targeting of intracellular cancer antigens, while chimeric antigen receptors (CAR) allow targeting of surface cancer or lineage specific antigens. Clinical responses have been observed with both approaches, and numerous further trials are underway.

Acute adverse events can occur following adoptive immunotherapy. Graft-versus-host disease (GvHD) is a common and serious complication of DLI. Administration of engineered T-cells has also resulted in toxicity. For instance, on-target off-tumour toxicity has been reported in native T-cell receptor transfer studies against melanoma antigens; T-cells re-directed to the renal cell carcinoma antigen carbonic anhydrase IX (CAIX) produced unexpected hepatotoxicity. Immune activation syndromes have been reported after CD19 CAR therapy. Finally vector-induced insertional mutagenesis results in a theoretical risk of lymphoproliferative disorders. The incidence and severity of these toxicities is unpredictable. Further, in contrast to a therapeutic protein or small molecules whose adverse events usually abate with the half-life of the therapeutic, T-cells engraft and replicate, potentially resulting in escalating and fulminant toxicity.

Suicide Genes

A suicide-gene is a genetically encoded mechanism which allows selective destruction of adoptively transferred cells, such as T-cells, in the face of unacceptable toxicity. Two suicide-genes have been tested in clinical studies: Herpes Simplex Virus thymidine kinase (HSV-TK) and inducible caspase 9 (iCasp9).

The herpes simplex virus I-derived thymidine kinase (HSV-TK) gene has been used as an in vivo suicide switch in donor T-cell infusions to treat recurrent malignancy and Epstein Barr virus (EBV) lymphoproliferation after hemopoietic stem cell transplantation. However, destruction of T cells causing graft-versus-host disease was incomplete, and the use of ganciclovir (or analogs) as a pro-drug to activate HSV-TK precludes administration of ganciclovir as an antiviral drug for cytomegalovirus infections. Moreover, HSV-TK-directed immune responses have resulted in elimination of HSV-TK-transduced cells, even in immunosuppressed human immunodeficiency virus and bone marrow transplant patients, compromising the persistence and hence efficacy of the infused T cells.

The activation mechanism behind Caspase 9 was exploited in the original iCasp9 molecule. All that is needed for Caspase 9 to become activated, is overcoming the energic barrier for Caspase 9 to homodimerize. The homodimer undergoes a conformational change and the proteolytic domain of one of a pair of dimers becomes active. Physiologically, this occurs by binding of the CARD domain of Caspase 9 to APAF-1. In iCasp9, the APAF-1 domain is replaced with a modified FKBP12 which has been mutated to selectively bind a chemical inducer of dimerization (CID). Presence of the CID results in homodimerization and activation. iCasp9 is based on a modified human caspase 9 fused to a human FK506 binding protein (FKBP) (Straathof et al (2005) Blood 105:4247-4254). It enables conditional dimerization in the presence of a small molecule CID, known as AP1903. AP1903 is an experimental drug and is considered biologically inert since it does not interact with wild-type FKBP12. However clinical experience with this agent is limited to a very small number of patients (Di Stasi, A. et al. (2011) N. Engl. J. Med. 365, 1673-1683; and Iuliucci, J. D. et al. (2001) J. Clin. Pharmacol. 41, 870-879). AP1903 is also a relatively large and polar molecule and unlikely to cross the blood-brain barrier.

In an alternative approach, executioner caspases can be activated by small molecules using a complex strategy which involves introduction of tobacco etch virus (TeV) proteolysis sites into Caspase 3 or 6 or 7 and co-expression with a split TEV protease which is recombined in the presence of rapamycin (Morgan et al (2014) Methods Enzymol. 544:179-213). This is an unsatisfactory strategy for a clinically useful suicide switch for a number of reasons: firstly three separate proteins are required which is highly complex: the modified caspase, and the two components of the split TeV protease respectively; secondly, TeV components are xenogeneic and likely immunogenic; finally, this strategy only activates protease sensitive caspase molecules which are downstream and less sensitive than apical caspases.

A suicide gene based on CID activation of FAS has been described (Amara et al (1999) Hum. Gene Ther. 10, 2651-2655). This also depends on this CID for activation, and since it does not directly activate the apoptosis cascade, escape (through FAS resistance) is possible.

A homodimerization system based on a standard pharmaceutical which replaces the need for an experimental CID would be an attractive alternative. However, no homodimerizing small molecule pharmaceuticals are available.

Other suicide genes have been proposed for instance full-length CD20 when expressed on a T-cell can render T-cells susceptible to lysis by the therapeutic anti-CD20 antibody Rituximab (Introna, M. et al. (2000) Hum. Gene Ther. 11, 611-620). Further suicide genes have also been described on this theme of antibody recognition, for example: RQR8 renders T-cells susceptible to CD20 but is more compact than the full-length CD20 molecule (Philip, B. et al. (2014) Blood doi:10.1182/blood-2014-01-545020); a truncated version of EGFR (huEGFRt) renders cells susceptible to lysis by anti-EGFR mAbs (Wang, X. et al. (2011) Blood 118, 1255-1263); and a myc epitope tag expressed on a cell surface leaves cells susceptible to lysis with an anti-myc antibody (Kieback et al (2008) Proc. Natl. Acad. Sci. U.S.A 105, 623-628). A major limitation of these antibody dependent approaches is their dependence on bioavailability of a therapeutic antibody at high local concentrations to act. It is known for instance that lytic antibodies are not particularly effective against bulky disease and a limitation of antibody based suicide genes is that cells resident where high antibody concentrations are not reached would escape. Further, in certain situations: for instance a severe macrophage activation syndrome or cytokine storm induced by a CAR T-cells; the additional immune activation induced by a monoclonal antibody may be deleterious to the clinical situation activation of the suicide gene is trying to treat.

There is thus a need for an alternative suicide gene which is not associated with the disadvantages mentioned above.

SUMMARY OF ASPECTS OF THE INVENTION

Figure 1:
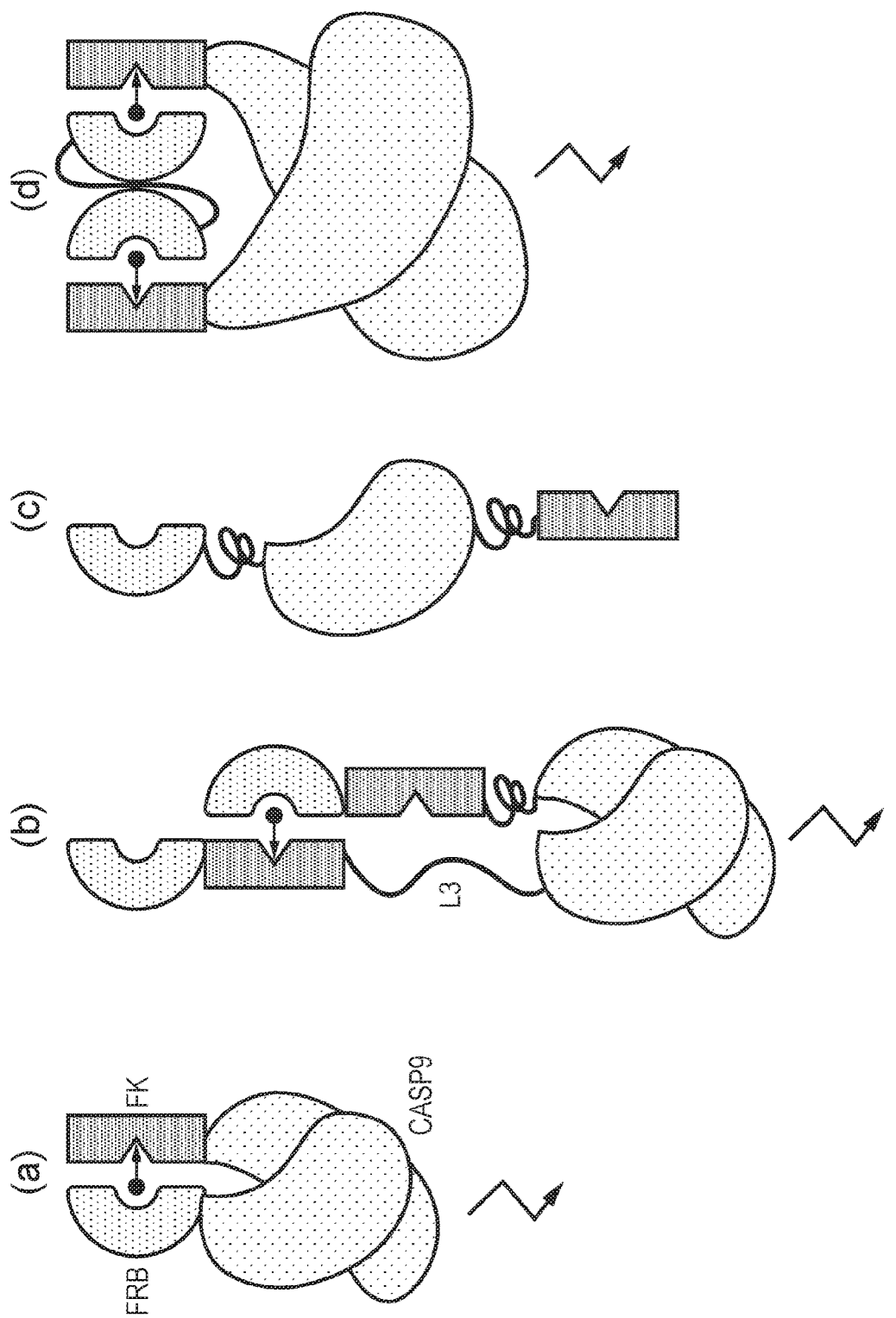
FIG. 1—Cartoons showing different approaches to Rap-Casp9. (a) Double construct where two molecules are expressed separately. Each molecule has the catalytic domain of Casp9 fused with either FKBP12 or FRB respectively. (b) Single construct where FKBP12 and FRB are directly fused together and then fused to the catalytic domain of Casp9 by a flexible linker. Self heterodimerization should not be possible in this orientation. (c) Single construct where the catalytic domain of Caspase 9 is flanked by FRB and FKBP12. Here, self heterodimerization may occur so this iteration is not expected to function well. (d) Double construct where the catalytic domain of Caspase 9 is fused to FKBP12 and a separate small protein which is a fusion of two copies of FRB is co-expressed.

The present inventors have developed a new suicide gene, which dimerizes in the presence of a chemical inducer of dimerization (CID) such as rapamycin or a rapamycin analogue.

Rapamycin and rapamycin analogues induce heterodimerisation by generating an interface between the FRB domain of mTOR and FKBP12. This association results in FKBP12 blocking access to the mTOR active site inhibiting its function. While mTOR is a very large protein, the precise small segment of mTOR required for interaction with Rapamycin is known and can be used.

The present inventors have shown that it is possible to use the heterodimerization mediated by rapamycin to induce homodimerization of a caspase. In particular, they have surprisingly shown that it is possible to create a multi-domain molecule, which includes (i) the FRB domain of mTOR; (ii) FKBP12; and (iii) a caspase, and use heterodimerization between the FRB domain of one copy of the molecule and the FKB12 domain of another copy of the molecule to cause homodimerization of the caspase domains.

Thus in a first embodiment of the first aspect of the invention, the present invention provides a chimeric protein having the formula:

Ht1-Ht2-Casp wherein
Casp is a caspase domain;
Ht1 is a first heterodimerization domain; and
Ht2 is a second heterodimerization domain
and wherein, in the presence of a chemical inducer of dimerization (CID), an identical pair of the chimeric proteins interact such that Ht1 from one chimeric protein heterodimerizes with Ht2 from the other chimeric protein, causing homodimerization of the two caspase domains.

The configuration is such that Ht1 does not heterodimerize to any significant extent with Ht2 within the same chimeric protein.

The caspase domain may comprise an initiator caspase selected from the following group: caspase-8, caspase-9 and caspase-10, or an executioner caspase selected from caspase-3 and caspase-7.

In the multi-domain protein of this first embodiment of the first aspect of the invention one heterodimerization domain may comprise an FK506-binding protein (FKBP) and the other heterodimerization domain may comprise an FRB domain of mTOR.

For this heterodimerization domain combination, a suitable CID is rapamycin or a rapamycin analog.

In a second embodiment of the first aspect of the invention there is provided a chimeric protein which comprises a caspase domain and a heterodimerization domain which comprises an FK506-binding protein (FKBP12), and a chimeric protein which comprises a caspase domain and a heterodimerization domain which comprises an FRB domain of mTOR.

In a third embodiment of this aspect of the invention there are provided two proteins:

Ht1-Casp and Ht2-Ht2 wherein Ht1-Casp is a chimeric protein comprising a caspase domain (Casp) and a first heterodimerization domain (Ht1); and Ht2-Ht2 is an interfacing protein comprising two or more second heterodimerization domains (Ht2); and
wherein, in the presence of a chemical inducer of dimerization (CID), a pair of the chimeric proteins Ht1-Casp9 interact such that Ht1 from each chimeric protein heterodimerizes with an Ht2 domain from the interfacing protein, causing homodimerization of the two caspase domains.

In a fourth embodiment of this aspect of the invention there is provided a chimeric protein having the formula:

Ht1-Casp-Ht2 wherein
Casp is a caspase domain;
Ht1 is a first heterodimerization domain; and
Ht2 is a second heterodimerization domain
and wherein, in the presence of a chemical inducer of dimerization (CID), an identical pair of the chimeric proteins interact such that Ht1 from one chimeric protein heterodimerizes with Ht2 from the other chimeric protein, causing homodimerization of the two caspase domains.

With this fourth embodiment of the first aspect of the invention, where one heterodimerization domain comprises an FK506-binding protein (FKBP) and the other heterodimerization domain comprises an FRB domain of mTOR and the CID is rapamycin or a derivative thereof, then concentrations of less that 5 nm, for example 1-3 nm or about 1 nm may be used in order to cause homodimerisation of the two caspase domains.

The chimeric protein may comprise a caspase domain fused to FKBP12 and is the interfacing protein may be a fusion of two or more FRB domains. These two or more FRB domains act as an interface, brining two FKBP12-Casp domains together.

In a second aspect, the present invention provides a nucleic acid sequence which encodes a chimeric protein according to the first aspect of the invention.

The nucleic acid may be in the form of a nucleic acid construct, which comprises a plurality of nucleic acid sequences. For example, the construct may comprise one or more nucleic acid sequence(s) according to the second aspect of the invention and a nucleic acid sequence encoding a T-cell receptor (TCR) or chimeric antigen receptor (CAR).

The nucleic acid construct may comprise:
i) a first nucleic acid sequence encoding a chimeric protein which comprises a caspase domain and a heterodimerization domain which comprises an FK506-binding protein (FKBP);
ii) a second nucleic acid sequence encoding a chimeric protein which comprises a caspase domain and a heterodimerization domain which comprises an FRB domain of mTOR.

There is also provided a nucleic acid construct having the structure:

Ht1-Casp-coexpr-Ht2-Ht2 wherein:
Casp is a nucleic acid sequence encoding a caspase domain;
Ht1 is a nucleic acid sequence encoding a first heterodimerization domain;
Ht2 is a nucleic acid sequence encoding a second heterodimerization domain; and
coexpr is a nucleic acid sequence allowing co-expression of Ht1-Casp and Ht2-Ht2,
wherein expression of the nucleic acid construct results in the production of a chimeric protein Ht1-Casp and an interfacing protein Ht2-Ht2 and wherein, in the presence of a chemical inducer of dimerization (CID), a pair of the chimeric proteins Ht1-Casp interact such that Ht1 from each chimeric protein heterodimerizes with an Ht2 domain from the interfacing protein, causing homodimerization of the two caspase domains.

Ht1 may comprise an FK506-binding protein (FKBP) and Ht2 may comprise an FRB domain of mTOR.

The nucleic acid construct may also comprise a nucleic acid sequence encoding a T-cell receptor (TCR) or chimeric antigen receptor (CAR).

In a third aspect, the present invention provides a vector which comprises a nucleic acid sequence or a nucleic acid construct according to the second aspect of the invention.

The vector which may also comprise a nucleotide of interest, such as a nucleotide sequence encoding a chimeric antigen receptor or a T-cell receptor, such that when the vector is used to transduce a target cell, the target cell co-expresses a chimeric protein according to the first aspect of the invention and a chimeric antigen receptor or T-cell receptor.

In a fourth aspect the present invention provides a cell which expresses a chimeric protein according to the first aspect of the invention.

The cell may comprise:
i) a first chimeric protein which comprises a caspase domain and a heterodimerization domain which comprises an FK506-binding protein (FKBP); and
ii) a second chimeric protein which comprises a caspase domain and a heterodimerization domain which comprises an FRB domain of mTOR.

There is also provided a cell which expresses two proteins:

Ht1-Casp and Ht2-Ht2 wherein Ht1-Casp is a chimeric protein comprising a caspase domain (Casp) and a first heterodimerization domain (Ht1); and Ht2-Ht2 is an interfacing protein comprising two second heterodimerization domains (Ht2); and
wherein, in the presence of a chemical inducer of dimerization (CID), a pair of the chimeric proteins Ht1-Casp9 interact such that Ht1 from each chimeric protein heterodimerizes with an Ht2 domain from the interfacing protein, causing homodimerization of the two caspase domains.

The cell may comprise a nucleic acid sequence or construct according to the second aspect of the invention.

The cell may, for example, be a haematopoietic stem cell, a lymphocyte or a T cell.

There is also provided a method for making a cell according to the fourth aspect of the invention which comprises the step of transducing or transfecting a cell with a vector according to the third aspect of the invention.

There is also provided a method for deleting a cell according to the fourth aspect of the invention, which comprises the step of exposing the cells to a chemical inducer of dimerization (CID).

The CID may be rapamycin or a rapamycin analog.

There is also provided a method for preventing or treating a disease in a subject, which comprises the step of administering a cell according to the fourth aspect of the invention to the subject.

The method may comprise the following steps:
(i) transducing or transfecting a sample of cells isolated from a subject with a vector according to the second aspect of the invention, and
(ii) administering the transduced/transfected cells to a patient.

The method may be for treating cancer.

There is also provided a method for preventing and/or treating an pathological immune reaction in a subject caused by administration of a cell according to the fourth aspect of the invention to the subject, which comprises the step of administering rapamycin or a rapamycin analog to the subject.

The pathological immune reaction may be selected from the following group: graft-versus-host disease; on-target, off-tumour toxicity; immune activation syndrome; and lymphoproliferative disorders.

The method for treating or prevention a disease in a subject may comprise the following steps:

(i) administering a cell according to the fourth aspect of the invention to the subject;

(ii) monitoring the subject for the development of a pathological immune reaction; and (iii) administering rapamycin or a rapamycin analog to the subject if the subject shows signs of developing or having developed a pathological immune reaction.

There is also provided a cell according to the fourth aspect of the invention for use in haematopoietic stem cell transplantation, lymphocyte infusion or adoptive cell transfer.

There is also provided rapamycin or a rapamycin analog for use in preventing or treating a pathological immune reaction caused by administration of a cell according to the fourth aspect of the invention to a subject.

Thus the present invention provides a suicide gene which allows the selective destruction of adoptively infused cells in the face of unacceptable toxicity, and which is activated by rapamycin and/or its analogues.

Rapamycin is standard pharmaceutical with well understood properties, excellent bioavailability and volume of distribution and which is widely available. Rapamycin also does not aggravate the condition being treated, in fact, as it is an immunosuppressant it is likely to have a beneficial effect on unwanted toxicity as well as its suicide gene function.

DETAILED DESCRIPTION

Chimeric Protein

The present invention relates to a chimeric protein which acts as a suicide gene. Cells expressing the chimeric protein may be deleted in vivo or in vitro by administration of a chemical inducer of dimerization (CID) such as rapamycin or a rapamycin analogue.

The chimeric protein may have the formula:

Ht1-Ht2-Casp in which

Casp is a caspase domain;
Ht1 is a first heterodimerization domain; and
Ht2 is a second heterodimerization domain.

The chimeric protein may have the formula:

Ht1-Ht2-L-Casp in which Casp, Ht1 and Ht2 are as defined above and L is an optional linker.

The configuration should be such that Ht1 does not significantly heterodimerize with Ht2 within the same chimeric protein molecule, but when two chimeric proteins come together in the presence of a chemical inducer of dimerization (CID) Ht1 from one chimeric protein heterodimerizes with Ht2 from the other chimeric protein, causing homodimerization of the two caspase domains.

The configuration is such that Ht1 does not heterodimerize to any significant extent with Ht2 within the same chimeric protein. For example, in a cell expressing a chimeric protein according to this embodiment of the first aspect of the invention, the presence of the CID should cause a greater proportion of dimerization between two chimeric proteins, than heterodimerization within the same chimeric protein. The amount of chimeric proteins which are heterodimerized within the same molecule in a cell or cell population, or in solution, may be less than 50%, 40%, 30%, 20%, 10%, 5% or 1% of the amount of chimeric proteins which are heterodimerized with a separate chimeric protein molecule, in the presence of the CID.

The chimeric protein may comprise the sequence shown as SEQ ID No. 1.

```
(FRB-FKBP12-L3-dCasp9)
                                                         SEQ ID No. 1
<----------------------FRB---------------------------------
MASRILWHEMWHEGLEEASRLYFGERNVKGMFEVLEPLHAMMERGPQTLKETSFNQAYGR -----------------FRB------------------><L1-><--FKBP12------
DLMEAQEWCRKYMKSGNVKDLLQAWDLYYHVFRRISKLEYSGGGSLEGVQVETISPGDGR -----------------FKBP12------------------------------------
TFPKRGQTCVVHYTGMLEDGKKFDSSRDRNKPFKFMLGKQEVIRGWEEGVAQMSVGQRAK ----------------------------------><------L3------><--dCasp9-
LTISPDYAYGATGHPGIIPPHATLVFDVELLKLESGGGGSGGGGSGGGGSGVDGFGDVGA -----------------------dCasp9------------------------------
LESLRGNADLAYILSMEPCGHCLIINNVNFCRESGLRTRTGSNIDCEKLRRRFSSLHFMV -----------------------dCasp9------------------------------
EVKGDLTAKKMVLALLELAQQDHGALDCCVVVILSHGCQASHLQFPGAVYGTDGCPVSVE -----------------------dCasp9------------------------------
KIVNIFNGTSCPSLGGKPKLFFIQACGGEQKDHGFEVASTSPEDESPGSNPEPDATPFQE -----------------------dCasp9------------------------------
GLRTFDQLDAISSLPTPSDIFVSYSTFPGFVSWRDPKSGSWYVETLDDIFEQWAHSEDLQ ---------------dCasp9----------------->
SLLLRVANAVSVKGIYKQMPGCFNFLRKKLFFKTSAS
```

In the above sequence "FKBP12" refers to the sequence of FKBP12; "dCasp9" refers to the catalytic domain of Casp9; "L1" is a one repeat linker; "FMD-2A" is a Foot and mouth disease 2A like peptide ERAV; "FRB" is the FRB domain of mTOR; "L3" is a two repeat linker; and "FRBw" is codon wobbled FRB In a second embodiment, the invention provides a "two-molecule" suicide gene system, in which the CID is rapamycin or a rapamycin analogue.

Thus, the present invention also provides i) a chimeric protein which comprises a caspase domain and a heterodimerization domain which comprises an FK506-binding protein (FKBP12); and ii) a chimeric protein which comprises a caspase domain and a heterodimerization domain which comprises an FRB domain of mTOR.

When a cell, such as a T-cell, expresses both these chimeric proteins, the presence of rapamycin or a rapamycin analogue causes the FKBP-comprising domain or i) to heterodimerise with the FRB-comprising domain or ii), thus causing homodimerization of the caspase domains from i) and ii).

In this embodiment of the invention, the chimeric protein may comprise the sequence shown as SEQ ID No. 2 or 3.

```
(FKBP12-dCasp9)
                                                           SEQ ID No. 2

<-------------------FKBP12----------------------------
MLEGVQVETISPGDGRTFPKRGQTCVVHYTGMLEDGKKFDSSRDRNKPFKFMLGKQEVIR

--------------------------FKBP12-----------------><L1-><----
GWEEGVAQMSVGQRAKLTISPDYAYGATGHPGIIPPHATLVFDVELLKLESGGGSGVDGF

----------------------dCasp9-------------------------------
GDVGALESLRGNADLAYILSMEPCGHCLIINNVNFCRESGLRTRTGSNIDCEKLRRRFSS ----------------------dCasp9-------------------------------
LHFMVEVKGDLTAKKMVLALLELAQQDHGALDCCVVVILSHGCQASHLQFPGAVYGTDGC ----------------------dCasp9-------------------------------
PVSVEKIVNIFNGTSCPSLGGKPKLFFIQACGGEQKDHGFEVASTSPEDESPGSNPEPDA ----------------------dCasp9-------------------------------
TPFQEGLRTFDQLDAISSLPTPSDIFVSYSTFPGFVSWRDPKSGSWYVETLDDIFEQWAH ----------------------dCasp9------------>
SEDLQSLLLRVANAVSVKGIYKQMPGCFNFLRKKLFFKTSAS (FRB-dCasp9)
                                                           SEQ ID No. 3

---------------------------FRB------------------------------>
MASRILWHEMWHEGLEEASRLYFGERNVKGMFEVLEPLHAMMERGPQTLKETSFNQAYGR

FRB              ><L1 ><    dCasp9
DLMEAQEWCRKYMKSGNVKDLLQAWDLYYHVFRRISKLEYSGGGSGVDGFGDVGALESLR ----------------------dCasp9-------------------------------
GNADLAYILSMEPCGHCLIINNVNFCRESGLRTRTGSNIDCEKLRRRFSSLHFMVEVKGD ----------------------dCasp9-------------------------------
LTAKKMVLALLELAQQDHGALDCCVVVILSHGCQASHLQFPGAVYGTDGCPVSVEKIVNI ----------------------dCasp9-------------------------------
FNGTSCPSLGGKPKLFFIQACGGEQKDHGFEVASTSPEDESPGSNPEPDATPFQEGLRTF ----------------------dCasp9-------------------------------
DQLDAISSLPTPSDIFVSYSTFPGFVSWRDPKSGSWYVETLDDIFEQWAHSEDLQSLLLR -------------dCasp9------------>
VANAVSVKGIYKQMPGCFNFLRKKLFFKTSAS
```

In a third embodiment, the invention provides an alternative "two molecule" approach, with a smaller footprint than the second embodiment. Here, Ht1 is fused with Caspase, and a second molecule comprises of Ht2-Ht2 fusion is co-expressed. In the presence of CID, Ht2-Ht2 brings together two Ht1-Casp molecules. In practise, this can be implemented by co-expressing FKBP12-Casp9 with FRB-FRB and activating with Rapamycin. Conveniently, these components can be co-expressed with a foot-and-mouth disease 2A like peptide. The second Ht2 (for example FRB) encoding sequence may be codon wobbled to prevent recombination.

Twelve caspases have been identified in humans. There are two types of apoptotic caspases: initiator caspases and executioner caspases. Initiator caspases, such as caspase-2, caspase-8, caspase-9, and caspase-10, cleave inactive pro-forms of effector caspases, thereby activating them. Executioner caspases, such as caspase-3, caspase-6 and caspase-7, then cleave other protein substrates within the cell, to trigger the apoptotic process.

The caspase domain of the chimeric protein of the first aspect of the present invention may comprise an initiator caspase selected from caspase-2; caspase-8, caspase-9 and caspase-10; or an executioner caspase selected from caspase-3, caspase-6 and caspase-7.

```
(FKBP12-dCasp9-2A-FRB-FRBw)
                                                         SEQ ID No. 4
<                   FKBP12
MLEGVQVETISPGDGRTFPKRGQTCVVHYTGMLEDGKKFDSSRDRNKPFKFMLGKQEVIR --------------------------FKBP12-----------------><L1-><----
GWEEGVAQMSVGQRAKLTISPDYAYGATGHPGIIPPHATLVFDVELLKLESGGGSGVDGF -----------------------dCasp9-------------------------------
GDVGALESLRGNADLAYILSMEPCGHCLIINNVNFCRESGLRTRTGSNIDCEKLRRRFSS -----------------------dCasp9-------------------------------
LHFMVEVKGDLTAKKMVLALLELAQQDHGALDCCVVVILSHGCQASHLQFPGAVYGTDGC -----------------------dCasp9-------------------------------
PVSVEKIVNIFNGTSCPSLGGKPKLFFIQACGGEQKDHGFEVASTSPEDESPGSNPEPDA -----------------------dCasp9-------------------------------
TPFQEGLRTFDQLDAISSLPTPSDIFVSYSTFPGFVSWRDPKSGSWYVETLDDIFEQWAH ------------dCasp9-----------------------><----FMD-2A-------
SEDLQSLLLRVANAVSVKGIYKQMPGCFNFLRKKLFFKTSASQCTNYALLKLAGDVESNP -><--------------------FRB----------------------------------
GPGVQVETISPGDGRTFPKRGQTCVVHYTGMLEDGKKVDSSRDRNKPFKFMLGKQEVIRG ---------------FRB------------------------------><----L2--->
WEEGVAQMSVGQRAKLTISPDYAYGATGHPGIIPPHATLVFDVELLKLESGGGGSGGGGS <---------------------------FRBw----------------------------
MLEGVQVETISPGDGRTFPKRGQTCVVHYTGMLEDGKKFDSSRDRNKPFKFMLGKQEVIR -----------------------FRBw----------------------->
GWEEGVAQMSVGQRAKLTISPDYAYGATGHPGIIPPHATLVFDVELLKLES
```

In the above sequence: "FKBP12" refers to FKBP12; "dCasp9" is the catalytic domain of Casp9; "L1" is a one repeat linker; "FMD-2A" is a Foot and mouth disease 2A like peptide ERAV; "FRB" is the FRB domain of mTOR; "L2" is a two repeat linker; and "FRBw" is codon wobbled FRB.

Caspase

Caspases, or cysteine-aspartic proteases or cysteine-dependent aspartate-directed proteases are a family of cysteine proteases that play essential roles in apoptosis.

In particular, the caspase domain of the chimeric protein of the first aspect of the present invention may comprise caspase-9. Caspase 9 is the key initiator caspase so its activation is a very sensitive trigger for apoptosis induction. Furthermore, homodimerization is all that is required for activation, rather than homodimerization and proteolytic cleavage.

Full length caspase-9 has the sequence shown as SEQ ID No. 5.

```
(Caspase-9)
                                                              SEQ ID No. 5
  1 MDEADRRLLR RCRLRLVEEL QVDQLVVDALL SSELFRPHMI EDIQRAGSGS RRDQARQLII

61 DLETRGSQAL PLFISCLEDT GQDMLASFLR TNRQAAKLSK PTLENLTPVV LRPEIRKPEV

121 LRPETPRPVD IGSGGFGDVG ALESLRGNAD LAYILSMEPC GHCLIINNVN FCRESGLRTR

181 TGSNIDCEKL RRRFSSPHFM VEVKGDLTAK KMVLALLELA QQDHGALDCC VVVILSHGCQ

241 ASHLQFPGAV YGTDGCPVSV EKIVNIFNGT SCPSLGGKPK LFFIQACGGE QKDHGFEVAS
```

```
301 TSPEDESPGS NPEPDATPFQ EGLRTFDQLD AISSLPTPSD IFVSYSTFPG FVSVVRDPKSG

361 SVVYVETLDDI FEQWAHSEDL QSLLLRVANA VSVKGIYKQM PGCFNFLRKK LFFKTS
```

Caspase-9 may be truncated, for example to remove the caspase recruitment domain. Truncated Caspase-9 is shown as SEQ ID No. 6

```
(truncated Caspase-9, lacking the CARD domain)
                                         SEQ ID No. 6
GFGDVGALESLRGNADLAYILSMEPCGHCLIINNVNFCRESGLRTRTGSN

IDCEKLRRRFSSLHFMVEVKGDLTAKKMVLALLELAQQDHGALDCCVVVI

LSHGCQASHLQFPGAVYGTDGCPVSVEKIVNIFNGTSCPSLGGKPKLFFI

QACGGEQKDHGFEVASTSPEDESPGSNPEPDATPFQEGLRTFDQLDAISS

LPTPSDIFVSYSTFPGFVSWRDPKSGSVVYVETLDDIFEQWAHSEDLQSL

LLRVANAVSVKGIYKQMPGCFNFLRKKLFFKTS
```

The chimeric protein of the first aspect of the invention may comprise SEQ ID No. 5 or SEQ ID No. 6 or a fragment or a variant thereof which retains the capacity to homodimerize and thus trigger apoptosis.

A variant caspase-9 sequence may have at least 80%, 85%, 90%, 95%, 98% or 99% sequence identity to SEQ ID No. 5 or 6.

The percentage identity between two polypeptide sequences may be readily determined by programs such as BLAST which is freely available at http://blast.ncbi.nlm.nih.gov.

In vivo, the protease caspase 9 is the central participant in a multi-component pathway known as the apoptosome, which controls cell deletion during embryogenesis, and physiological responses that trigger cell death as well as lethal cellular insults such as ionizing radiation or chemotherapeutic drugs. The function of caspase 9 is to generate the active forms of caspases 3 and 7 by limited proteolysis, and thereby transmit the apoptotic signal to the execution phase. However, caspase 9 is unusual among its close relatives in that proteolysis between the large and small subunit does not convert the latent zymogen to the catalytic form. In fact, it is homodimerization which is required for activation.

Heterodimerization Domains

The macrolides rapamycin and FK506 act by inducing the heterodimerization of cellular proteins. Each drug binds with a high affinity to the FKBP12 protein, creating a drug-protein complex that subsequently binds and inactivates mTOR/FRAP and calcineurin, respectively. The FKBP-rapamycin binding (FRB) domain of mTOR has been defined and applied as an isolated 89 amino acid protein moiety that can be fused to a protein of interest. Rapamycin can then induce the approximation of FRB fusions to FKBP12 or proteins fused with FKBP 12.

In the context of the present invention one of the heterodimerization domains (Ht1 or Ht2) may be or comprise FRB, or a variant thereof and the other heterodimerization domain (Ht2 or Ht1) may be or comprise FKBP12 or a variant thereof.

Rapamycin has several properties of an ideal dimerizer: it has a high affinity (KD<1 nM) for FRB when bound to FKBP12, and is highly specific for the FRB domain of mTOR. Rapamycin is an effective therapeutic immunosuppressant with a favourable pharmacokinetic and pharmacodynamics profile in mammals. Pharmacological analogues of Rapamycin with different pharmacokinetic and dynamic properties such as Everolimus, Temsirolimus and Deforolimus (Benjamin et al, Nature Reviews, Drug Discovery, 2011) may also be used according to the clinical setting.

In order to prevent rapamycin binding and inactivating endogenous mTOR, the surface of rapamycin which contacts FRB may be modified. Compensatory mutation of the FRB domain to form a burface that accommodates the "bumped" rapamycin restores dimerizing interactions only with the FRB mutant and not to the endogenous mTOR protein.

Figure 3:
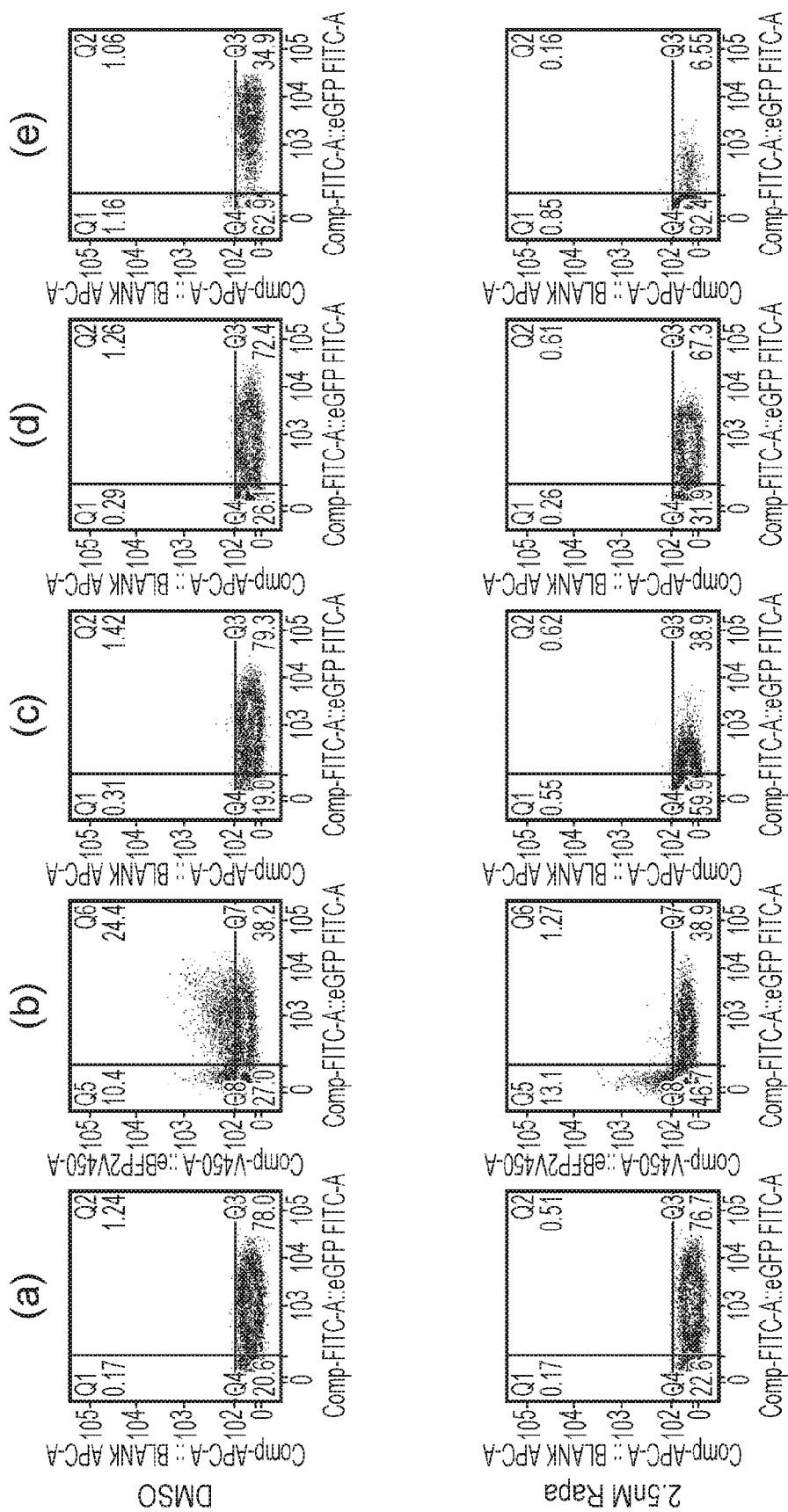
FIG. 3—Function of RapCasp9 variants. T-cells were transduced with (a) eGFP alone; (b) double transduced with FKBP12-Casp9 and FRB-Casp9 co-expressed with eGFP and eBFP2 respectively; (c) transduced with FRB-FKBP12-Casp9 and (d) transduced with FRB-Casp9-FKBP12 and (e) FBP12-Casp9-2A-FRB-FRBw. Only a proportion of cells were transduced, the negative cells acted as an internal negative control. T-cells were exposed for 48 hours to 2.5 nM Rapamycin. T-cells were then stained with Annexin-V and 7AAD and analysed by flow-cytometry. eGFP vs eBFP2 is shown on live cells as determined by Annexin-V and 7AAD staining.

Bayle et al. (Chem Bio; 2006; 13; 99-107) describes various rapamycin analogs, or "rapalogs" and their corresponding modified FRB binding domains. For example, Bayle et al. (2006) describes the rapalogs: C-20-methyllyrlrapamycin (MaRap), C16(S)-Butylsulfonamidorapamycin (C16-BS-Rap) and C16-(S)-7-methylindolerapamycin (AP-21976/C16-AiRap), as shown in FIG. 3, in combination with the respective complementary binding domains for each. Other rapamycins/rapalogs include sirolimus and tacrolimus.

The heterodimerization domains of the chimeric protein may be or comprise one the sequences shown as SEQ ID NO: 7 to SEQ ID NO: 11, or a variant thereof.

SEQ ID No 7—FKBP12 domain
MGVQVETISPGDGRTFPKRGQTCVVHYTGMLEDGKKFDSSRDRNKPFKFMLGKQEVIRGWEEGVAQMSVGQRAKLTISPDYAYGATGHPGIIPPHATLVFDVELLKLE SEQ ID No 8—wild-type FRB segment of mTOR MASRILWHEMWHEGLEEASRLYFGERNVKGMFEVLEPLHAMMERGPQTLKETSFNQAYGRDLMEAQEWCRKYMKSGNVKDLTQAWDLYYHVFRRISKLES SEQ ID No 9—FRB with T to L substitution at 2098 which allows binding to AP21967 MASRILWHEMWHEGLEEASRLYFGERNVKGMFEVLEPLHAMMERGPQTLKETSFNQAYGRDLMEAQEWCRKYMKSGNVKDLLQAWDLYYHVFRRISKLES SEQ ID No 10—FRB segment of mTOR with T to H substitution at 2098 and to W at F at residue 2101 of the full mTOR which binds Rapamycin with reduced affinity to wild type MASRILWHEMWHEGLEEASRLYFGERNVKGMFEVLEPLHAMMERGPQTLKETSFN QAYGRDLME- AQEWCRKYMKSGNVKDLHQAFDLYYHVFRRISKLES SEQ ID No 11—FRB segment of mTOR with K to P substitution at residue 2095 of the full mTOR which binds Rapamycin with reduced affinity MASRILWHEMWHEGLEEASRLYFGERNVKGMFEVLEPLHAMMERGPQTLKETSFN QAYGRDLMEAQEWCRKYMKSGNVPDLTQAWDLYYHVFRRISKLES Variant sequences may have at least 80%, 85%, 90%, 95%, 98% or 99% sequence identity to SEQ ID No. 7 to 11, provided that the sequences provide an effective dimerization system. That is, provided that the sequences facilitate sufficient co-localisation of the two chimeric proteins to allow homodimerization of the two caspase domains.

The "wild-type" FRB domain shown as SEQ ID No. 8 comprises amino acids 2025-2114 of human mTOR. Using the amino acid numbering system of human mTOR, the FRB sequence of the chimeric protein of the invention may comprise an amino acid substitution at one of more of the following positions: 2095, 2098, 2101.

The variant FRB used in the chimeric protein of the invention may comprise one of the following amino acids at positions 2095, 2098 and 2101:

2095: K, P, T or A
2098: T, L, H or F
2101: W or F

Bayle et al (as above) describe the following FRB variants, annotated according to the amino acids at positions 2095, 2098 and 2101 (see Table 1): KTW, PLF, KLW, PLW, TLW, ALW, PTF, ATF, TTF, KLF, PLF, TLF, ALF, KTF, KHF, KFF, KLF. These variants are capable of binding rapamycin and rapalogs to varying extents, as shown in Table 1 and FIG. 5A of Bayle et al. The chimeric protein of the invention may comprise one of these FRB variants.

Linker

A linker may be included to spatially separate the caspase domain and the heterodimerization domain(s).

In the first embodiment of the first aspect of the present invention, the chimeric protein comprises two heterodimerization domains which are held in a configuration such that they cannot heterodimerize with each other in the presence of the CID in a single molecule, but Ht1 on one molecule can heterodimerise with Ht2 on another chimeric molecule having the same heterodimerization domains (FIG. 1B). In a design where Ht1 and Ht2 flank the Caspase domain (Ht1-Casp-Ht2), activation was inferior to designs where Ht1 and Ht2 were linked together, indicating the importance of preventing non-productive binding of Ht1 and Ht2 from a single molecule to a single CID.

In this embodiment, the linker (L1) should provide sufficient flexibility so that the catalytic domains can homodimerize, but not so much flexibility that the energic barrier to homodimerization is not overcome (FIG. 1). For example, the linker may be less than 15, less than 10 or between 5-15 or 5-10 amino acids in length.

In the second embodiment of the first aspect of the present invention, the chimeric protein comprises a single heterodimerization domain, which is capable of heterodimerization with a complementary heterodimerization domain on a second chimeric protein in the presence of a CID.

In an alternative configuration, the two heterodimerisation domains may be provided on a single molecule with a long linker (L2), providing a construct having the formula:

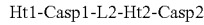

Ht1-Casp1-L2-Ht2-Casp2

The HT and Casp domains may be in either order on each side of the linker.

In this embodiment, the linker L2 may confer sufficient flexibility so the first heterodimerization domain can heterodimerize with the second heterodimerization domain; and so that the caspase domain in the part of the molecule corresponding to the 'first chimeric protein' can homodimerize with the caspase domain in the part of the molecule corresponding to the 'second chimeric protein'.

In the third embodiment of the first aspect of the invention, Casp is fused to a single heterodimerization domain, but a second molecule which is a fusion of two or more copies of the other heterodimerization domain. The two molecules may be co-expressed. In this case, the second molecule acts as an interface bringing two or more Casp domains together in the presence of CID. In this case, the two or more copies of heterodimerization domains must be fused in such a way to allow approximation of the Casp9 domains sufficiently to activate them.

The interfacing protein may be multimeric, comprising more than two Ht2 domains. For example, it is possible to combine a plurality of Ht2 domains in a single interfacing protein using a multimerising linker such as a coiled coil domain.

In this embodiment the interfacing protein may have the formula Ht2-L2-Ht2, or Ht2-L2 in which L2 is a coiled-coil domain.

A coiled coil is a structural motif in which two to seven alpha-helices are wrapped together like the strands of a rope. The structure of coiled coil domains is well known in the art. For example as described by Lupas & Gruber (Advances in Protein Chemistry; 2007; 70; 37-38).

Coiled coils usually contain a repeated pattern, hxxhcxc, of hydrophobic (h) and charged (c) amino-acid residues, referred to as a heptad repeat. The positions in the heptad repeat are usually labeled abcdefg, where a and d are the hydrophobic positions, often being occupied by isoleucine, leucine, or valine. Folding a sequence with this repeating pattern into an alpha-helical secondary structure causes the hydrophobic residues to be presented as a 'stripe' that coils gently around the helix in left-handed fashion, forming an amphipathic structure. The most favourable way for two such helices to arrange themselves in the cytoplasm is to wrap the hydrophobic strands against each other sandwiched between the hydrophilic amino acids. Thus, it is the burial of hydrophobic surfaces that provides the thermodynamic driving force for the oligomerization. The packing in a coiled-coil interface is exceptionally tight, with almost complete van der Waals contact between the side-chains of the a and d residues.

Examples of proteins which contain a coiled coil domain include, but are not limited to, kinesin motor protein, hepatitis D delta antigen, archaeal box C/D sRNP core protein, cartilage-oligomeric matrix protein (COMP), mannose-binding protein A, coiled-coil serine-rich protein 1, polypeptide release factor 2, SNAP-25, SNARE, Lac repressor or apolipoprotein E.

Chemical Inducer of Dimerization (CID)

The chemical inducer of dimerization (CID) may be any molecule which induces heterodimerization between Ht1 and Ht2 on separate chimeric molecules having the same Ht1 and Ht2 domains.

Figure 4:
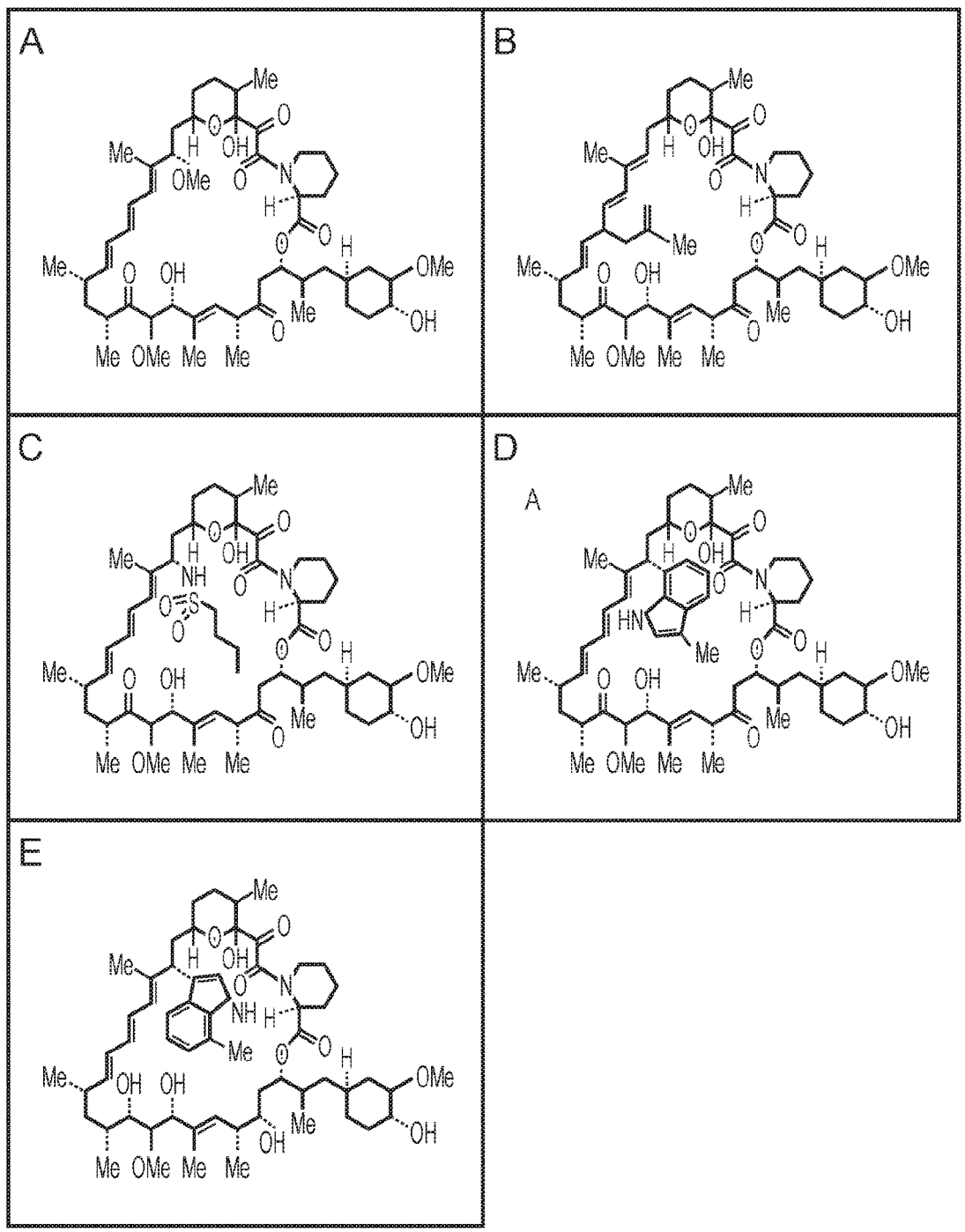
FIG. 4—Rapamycin and rapalogs. A) Rapamycin; B) C-20-methyllyrlrapamycin (MaRap); C) C16(S)-Butylsulfonamidorapamycin (C16-BS-Rap); D) C16-(S)-3-mehylindolerapamycin (C16-iRap); and E) C16-(S)-7-methylindolerapamycin (AP21976/C16-AiRap).

The CID may be rapamycin or a rapamycin analog ("rapalogs") which have improved or differing pharmadynamic or pharmacokinetic properties to rapamycin but have the same broad mechanism of action. The CID may be an altered rapamycin with engineered specificity for complementary FKBP12 or FRB—for example as shown in FIG. 4. Bayle et al (2006, as above) describes various rapalogs functionalised at C16 and/or C20.

Examples of such rapalogs in the first category include Sirolimus, Everolimus, Temsirolimus and Deforolimus. Examples of rapalogs in the second category include C-20-methyllyrlrapamycin (MaRap); C16(S)-Butylsulfonamidorapamycin (C16-BS-Rap); C16-(S)-3-mehylindolerapamycin (C16-iRap); and C16-(S)-7-methylindolerapamycin (AP2-1976/C16-AiRap).

Homodimerisation of the caspase domains in the presence of CID may result in caspase activation which is 2, 5, 10, 50, 100, 1,000 or 10,000-fold higher than the caspase activity which occurs in the absence of CID.

Rapamycin is a potent immunsuppressive agent. Analogues of rapamycin (rapalogues) are in every day clinical use. Modern rapalogues have excellent bioavailability and volumes of distribution. Although they are potent immunsuppressive agents, a short dose (to activate a suicide gene)

should have minimal side-effects. Further, unlike administration of a mAb, the pharmacological effects of rapamycin and analogues may well be advantageous in clinical scenarios where suicide genes require activation, such as off-tumour toxicity or immune hyperactivation syndromes.

Nucleic Acid Sequences

The second aspect of the invention provides a nucleic acid sequence which encodes a chimeric protein according to the invention.

As used herein, the terms "polynucleotide", "nucleotide", and "nucleic acid" are intended to be synonymous with each other.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

Nucleic acids according to the second aspect of the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the use as described herein, it is to be understood that the polynucleotides may be modified by any method available in the art. Such modifications may be carried out in order to enhance the in vivo activity or life span of polynucleotides of interest.

The terms "variant", "homologue" or "derivative" in relation to a nucleotide sequence include any substitution of, variation of, modification of, replacement of, deletion of or addition of one (or more) nucleic acid from or to the sequence.

In the first embodiment of this aspect of the invention there is provided a nucleic acid which encodes a chimeric protein having the formula:

Ht1-Ht2-L-Casp wherein
Ht1 is a first heterodimerization domain; and
Ht2 is a second heterodimerization domain.
L is an optional linker;
Casp is a caspase domain;

The nucleic acid sequence may encode the chimeric protein sequence shown as SEQ ID No. 1 or a variant thereof.

For example the nucleotide sequence may comprise the sequence shown as SEQ ID No. 12

(FRB-FKBP12-L3-Casp9)
SEQ ID No. 12
ATGGCTTCTAGAATCCTCTGGCATGAGATGTGGCATGAAGGCCTGGAAGA

GGCATCTCGTTTGTACTTTGGGGAAAGGAACGTGAAAGGCATGTTTGAGG

TGCTGGAGCCCTTGCATGCTATGATGGAACGGGGCCCCCAGACTCTGAAG

GAAACATCCTTTAATCAGGCCTATGGTCGAGATTTAATGGAGGCCCAAGA

GTGGTGCAGGAAGTACATGAAATCAGGGAATGTCAAGGACCTCCTCCAAG

-continued
CCTGGGACCTCTATTATCATGTGTTCCGACGAATCTCAAAGCTCGAGTAT

AGCGGCGGCGGCAGCCTGGAGGGCGTGCAGGTGGAGACCATCAGCCCAGG

CGACGGCAGAACCTTCCCCAAGAGAGGCCAGACCTGCGTGGTGCACTATA

CCGGCATGCTGGAGGACGGCAAGAAGTTCGACAGCAGCCGCGACCGCAAT

AAGCCCTTCAAGTTCATGCTGGGCAAGCAGGAGGTGATCAGAGGCTGGGA

GGAGGGCGTGGCCCAGATGAGCGTGGGCCAGAGAGCCAAGCTGACCATCA

GCCCCGACTACGCCTATGGCGCCACCGGCCACCCCGGCATCATCCCACCC

CACGCCACCCTGGTGTTTGATGTGGAGCTGCTGAAGCTGGAGTCCGGCGG

AGGCGGGTCTGGAGGAGGCGGCAGCGGCGGCGGCGGGTCAGGCGTGGATG

GCTTCGGCGACGTGGGAGCCCTGGAGAGCCTGAGAGGCAACGCCGATCTG

GCCTACATCCTGAGCATGGAGCCCTGTGGCCACTGCCTGATCATCAACAA

CGTGAACTTCTGCCGGGAGAGCGGCCTGCGGACCCGGACCGGCAGCAACA

TCGACTGCGAGAAGCTGAGGAGGCGCTTCTCCTCCCTGCACTTTATGGTG

GAGGTGAAAGGCGATCTGACTGCCAAGAAAATGGTGCTGGCCCTGCTGGA

GCTGGCCCAGCACCACCACGCACCCCTCCATTGCTCTCTCGTCCTCATCC

TCTCCCACCCCTCCCACCCCAGCCACCTGCAGTTCCCCGGAGCCGTGTAC

GGCACCGACGGCTGTCCCGTGTCCGTGGAGAAGATCGTGAACATCTTCAA

CGGCACCTCCTGCCCCTCCCTGGGCGGCAAGCCCAAGCTGTTCTTTATCC

AGGCCTGTGGCGGCGAGCAGAAGGACCACGGCTTTGAGGTGGCCAGCACC

TCCCCCGAGGACGAGAGCCCAGGCAGCAACCCCGAGCCCGACGCCACCCC

CTTCCAGGAGGGCCTGCGCACCTTCGACCAGCTGGACGCCATCAGCAGCC

TGCCCACCCCCAGCGACATCTTCGTGAGCTACAGCACCTTTCCCGGCTTC

GTGAGCTGGCGCGATCCCAAGTCCGGCTCTTGGTATGTGGAGACCCTGGA

CGACATCTTTGAGCAGTGGGCTCATAGCGAGGACCTGCAGAGCCTGCTGC

TGCGCGTGGCCAATGCCGTGAGCGTGAAGGGCATCTACAAGCAGATGCCA

GGCTGCTTCAACTTCCTGCGGAAGAAGCTGTTCTTCAAGACCAGCGCCTC

CTGA

In a second embodiment of this aspect of the invention there is provided a nucleic acid sequence encoding a chimeric protein having the formula:

Ht1-L-Casp wherein
Ht1 is a heterodimerization domain.
L is an optional linker; and
Casp is a caspase domain;

The nucleic acid sequence may encode the chimeric protein sequence shown as SEQ ID No. 2 or 3 or a variant thereof.

For example the nucleotide sequence may comprise the sequence shown as SEQ ID No. 13 or 14

(FKBP12-dCasp9)
SEQ ID No. 13
ATGCTGGAGGGCGTGCAGGTGGAGACCATCAGCCCAGGCGACGGCAGAAC

CTTCCCCAAGAGAGGCCAGACCTGCGTGGTGCACTATACCGGCATGCTGG

AGGACGGCAAGAAGTTCGACAGCAGCCGCGACCGCAATAAGCCCTTCAAG

-continued

TTCATGCTGGGCAAGCAGGAGGTGATCAGAGGCTGGGAGGAGGGCGTGGC

CCAGATGAGCGTGGGCCAGAGAGCCAAGCTGACCATCAGCCCCGACTACG

CCTATGGCGCCACCGGCCACCCCGGCATCATCCCACCCCACGCCACCCTG

GTGTTTGATGTGGAGCTGCTGAAGCTGGAGTCCGGAGGCGGCTCCGGCGT

GGATGGCTTCGGCGACGTGGGAGCCCTGGAGAGCCTGAGAGGCAACGCCG

ATCTGGCCTACATCCTGAGCATGGAGCCCTGTGGCCACTGCCTGATCATC

AACAACGTGAACTTCTGCCGGGAGAGCGGCCTGCGGACCCGGACCGGCAG

CAACATCGACTGCGAGAAGCTGAGGAGGCGCTTCTCCTCCCTGCACTTTA

TGGTGGAGGTGAAAGGCGATCTGACTGCCAAGAAAATGGTGCTGGCCCTG

CTGGAGCTGGCCCAGCAGGACCACGGAGCCCTGGATTGCTGTGTGGTGGT

GATCCTGTCCCACGGCTGCCAGGCCAGCCACCTGCAGTTCCCCGGAGCCG

TGTACGGCACCGACGGCTGTCCCGTGTCCGTGGAAGATCGTGAACATC

TTCAACGGCACCTCCTGCCCCTCCCTGGGCGGCAAGCCCAAGCTGTTCTT

TATCCAGGCCTGTGGCGGCGAGCAGAAGGACCACGGCTTTGAGGTGGCCA

GCACCTCCCCCGAGGACGAGAGCCCAGGCAGCAACCCCGAGCCCGACGCC

ACCCCCTTCCAGGAGGGCCTGCGCACCTTCGACCAGCTGGACGCCATCAG

CAGCCTGCCCACCCCCAGCGACATCTTCGTGAGCTACAGCACCTTTCCCG

GCTTCGTGAGCTGGCGCGATCCCAAGTCCGGCTCTTGGTATGTGGAGACC

CTGGACGACATCTTTGAGCAGTGGGCTCATAGCGAGGACCTGCAGAGCCT

GCTGCTGCGCGTGGCCAATGCCGTGAGCGTGAAGGGCATCTACAAGCAGA

TGCCAGGCTGCTTCAACTTCCTGCGGAAGAAGCTGTTCTTCAAGACCAGC

GCCTCCTGA (FRB-dCasp9)

SEQ ID No. 14

ATGGCTTCTAGAATCCTCTGGCATGAGATGTGGCATGAAGGCCTGGAAGA

GGCATCTCGTTTGTACTTTGGGGAAAGGAACGTGAAAGGCATGTTTGAGG

TGCTGGAGCCCTTGCATGCTATGATGGAACGGGGCCCCCAGACTCTGAAG

GAAACATCCTTTAATCAGGCCTATGGTCGAGATTTAATGGAGGCCCAAGA

GTGGTGCAGGAAGTACATGAAATCAGGGAATGTCAAGGACCTCCTCCAAG

CCTGGGACCTCTATTATCATGTGTTCCGACGAATCTCAAAGCTCGAGTAT

AGCGGCGGCGGCAGCGGCGTGGATGGCTTCGGCGACGTGGGAGCCCTGGA

GAGCCTGAGAGGCAACGCCGATCTGGCCTACATCCTGAGCATGGAGCCCT

GTGGCCACTGCCTGATCATCAACAACGTGAACTTCTGCCGGGAGAGCGGC

CTGCGGACCCGGACCGGCAGCAACATCGACTGCGAGAAGCTGAGGAGGCG

CTTCTCCTCCCTGCACTTTATGGTGGAGGTGAAAGGCGATCTGACTGCCA

AGAAAATGGTGCTGGCCCTGCTGGAGCTGGCCCAGCAGGACCACGGAGCC

CTCCATTCCTCTCTCCTCCTCATCCTCTCCCACCCCTCCCACCCCAGCCA

CCTCCACTTCCCCCCACCCGTCTACCCCACCCACCCCTCTCCCCTCTCCC

TCCACAACATCGTCAACATCTTCAACGGCACCTCCTGCCCCTCCCTGGGC

GGCAAGCCCAAGCTGTTCTTTATCCAGGCCTGTGGCGGCGAGCAGAAGGA

CCACGGCTTTGAGGTGGCCAGCACCTCCCCCGAGGACGAGAGCCCAGGCA

GCAACCCCGAGCCCGACGCCACCCCCTTCCAGGAGGGCCTGCGCACCTTC

GACCAGCTGGACGCCATCAGCAGCCTGCCCACCCCCAGCGACATCTTCGT

GAGCTACAGCACCTTTCCCGGCTTCGTGAGCTGGCGCGATCCCAAGTCCG

GCTCTTGGTATGTGGAGACCTGGACGACATCTTTGAGCAGTGGGCTCAT

AGCGAGGACCTGCAGAGCCTGCTGCTGCGCGTGGCCAATGCCGTGAGCGT

GAAGGGCATCTACAAGCAGATGCCAGGCTGCTTCAACTTCCTGCGGAAGA

AGCTGTTCTTCAAGACCAGCGCCTCCTGA.

In this second embodiment, the nucleic acid sequences may be provided in the form of a construct which encodes both chimeric proteins.

The construct may encode a polyprotein having the formula:

Ht1-L2-Casp-coexpr-Ht2-L2-Casp wherein
Ht1 is a first heterodimerization domain;
L1 and L2 are optional linkers which may be the same or different;
Coexpr is a sequence enabling coexpression of the two proteins: Ht1-L1-Casp and Ht2-L2-Casp;
Ht2 is a second heterodimerization domain; and
Casp is a caspase domain.

Where there are nucleic acid sequences encoding the same or similar sequences, such as the two caspase domains, one of the sequences may be codon wobbled to avoid homologous recombination.

In a third embodiment, nucleic acid sequence is provided which encodes a sequence with the following formula:

Ht1-Casp-coexpr-Ht2-Ht2 wherein
Casp is a caspase domain;
Ht1 is a first heterodimerization domain;
Coexpr is a sequence enabling coexpression of the proteins Ht1-Casp and Ht2-Ht2, such as a cleavage site; and
Ht2 is a second heterodimerisation domain, which heterodimerises with Ht1 in the presence of a chemical inducer of dimerization (CID).

In the sequence encoding the second protein, Ht2-Ht2, one of the sequences encoding Ht2 may be codon wobbled, in order to avoid homologous recombination.

The nucleic acid construct according to the third embodiment may have the sequence shown as SEQ ID No. 15.

(FKBP12-Casp9-2A-FRB-FRBw)

SEQ ID No. 15

ATGCTGGAGGGCGTGCAGGTGGAGACCATCAGCCCAGGCGACGGCAGAAC

CTTCCCCAAGAGAGGCCAGACCTGCGTGGTGCACTATACCGGCATGCTGG

AGGACGGCAAGAAGTTCGACAGCAGCCGCGACCGCAATAAGCCCTTCAAG

TTCATGCTGGGCAAGCAGGAGGTGATCAGAGGCTGGGAGGAGGGCGTGGC

CCAGATGAGCGTGGGCCAGAGAGCCAAGCTGACCATCAGCCCCGACTACG

CCTATGGCGCCACCGGCCACCCCGGCATCATCCCACCCCACGCCACCCTG

GTGTTTGATGTGGAGCTGCTGAAGCTGGAGTCCGGAGGCGGCTCCGGCGT

GGATGGCTTCGGCGACGTGGGAGCCCTGGAGAGCCTGAGAGGCAACGCCG

ATCTGGCCTACATCCTGAGCATGGAGCCCTGTGGCCACTGCCTGATCATC

```
-continued
AACAACGTGAACTTCTGCCGGGAGAGCGGCCTGCGGACCCGGACCGGCAG

CAACATCGACTGCGAGAAGCTGAGGAGGCGCTTCTCCTCCCTGCACTTTA

TGGTGGAGGTGAAAGGCGATCTGACTGCCAAGAAAATGGTGCTGGCCCTG

CTGGAGCTGGCCCAGCAGGACCACGGAGCCCTGGATTGCTGTGTGGTGGT

GATCCTGTCCCACGGCTGCCAGGCCAGCCACCTGCAGTTCCCCGGAGCCG

TGTACGGCACCGACGGCTGTCCCGTGTCCGTGGAGAAGATCGTGAACATC

TTCAACGGCACCTCCTGCCCCTCCCTGGGCGGCAAGCCCAAGCTGTTCTT

TATCCAGGCCTGTGGCGGCGAGCAGAAGGACCACGGCTTTGAGGTGGCCA

GCACCTCCCCCGAGGACGAGAGCCCAGGCAGCAACCCCGAGCCCGACGCC

ACCCCCTTCCACCACCCCTCCGCACCTTCGACCACCTGCACCCCATCAC

CACCCTCCCCACCCCCAGCGACATCTTCGTGAGCTACAGCACCTTTCCCG

GCTTCGTGAGCTGGCGCGATCCCAAGTCCGGCTCTTGGTATGTGGAGACC

CTGGACGACATCTTTGAGCAGTGGGCTCATAGCGAGGACCTGCAGAGCCT

GCTGCTGCGCGTGGCCAATGCCGTGAGCGTGAAGGGCATCTACAAGCAGA

TGCCAGGCTGCTTCAACTTCCTGCGGAAGAAGCTGTTCTTCAAGACCAGC

GCCTCCCAGTGCACCAATTATGCTTTGCTTAAGCTGGCAGGCGATGTGGA

ATCAAACCCGGGTCCTGGGGTACAGGTGGAGACCATCTCTCCTGGCGACG

GGAGAACATTTCCTAAAAGGGGCCAAACATGCGTGGTTCACTATACCGGT

ATGCTGGAGGATGGCAAAAAAGTAGACTCCAGCCGGGATAGAAACAAACC

CTTTAAGTTCATGCTGGGTAAGCAGGAAGTTATACGGGGCTGGGAAGAGG

GAGTAGCTCAGATGTCTGTGGGCCAGAGGGCCAAGCTGACCATCTCACCG

GACTACGCCTACGGCGCTACCGGCCACCCTGGCATTATACCACCCCATGC

AACTCTCGTCTTCGATGTTGAGTTGCTCAAACTGGAATCAGGCGGAGGCG

GGTCTGGAGGAGGCGGCAGCATGCTGGAGGGCGTGCAGGTGGAGACCATC

AGCCCAGGCGACGGCAGAACCTTCCCCAAGAGAGGCCAGACCTGCGTGGT

GCACTATACCGGCATGCTGGAGGACGGCAAGAAGTTCGACAGCAGCCGCG

ACCGCAATAAGCCCTTCAAGTTCATGCTGGGCAAGCAGGAGGTGATCAGA

GGCTGGGAGGAGGGCGTGGCCCAGATGAGCGTGGGCCAGAGAGCCAAGCT

GACCATCAGCCCCGACTACGCCTATGGCGCCACCGCCCACCCCCGCATCA

TCCCACCCCACGCCACCCTGGTGTTTGATGTGGAGCTGCTGAAGCTGGAG

TCCTGA
```

Nucleic acid sequences with a high degree of similarity, such as the caspase sequence(s) or FRB sequences may be codon wobbled to avoid recombination.

Nucleic Acid Construct

The invention also provides a nucleic acid construct which comprises:
  i) a first nucleic acid sequence encoding a chimeric protein which comprises a caspase domain and a heterodimerization domain which comprises an FK506-binding protein (FKBP); and
  ii) a second nucleic acid sequence encoding a chimeric protein which comprises a caspase domain and a heterodimerization domain which comprises an FRB domain of mTOR.

The invention also provides a nucleic acid construct which comprises a nucleic acid sequence encoding one or more chimeric protein(s) and a further nucleic acid sequence of interest (NOI). The NOI may, for example encode a T-cell receptor (TCR) or chimeric antigen receptor (CAR).

The nucleic acid sequences may be joined by a sequence allowing co-expression of the two or more nucleic acid sequences. For example, the construct may comprise an internal promoter, an internal ribosome entry sequence (IRES) sequence or a sequence encoding a cleavage site. The cleavage site may be self-cleaving, such that when the polypeptide is produced, it is immediately cleaved into the discrete proteins without the need for any external cleavage activity.

Various self-cleaving sites are known, including the Foot-and-Mouth disease virus (FMDV) 2a self-cleaving peptide, which has the sequence shown as SEQ ID No. 16 or 17:

SEQ ID No. 16
RAEGRGSLLTCGDVEENPGP.

or

SEQ ID No 17
QCTNYALLKLAGDVESNPGP

The co-expressing sequence may be an internal ribosome entry sequence (IRES). The co-expressing sequence may be an internal promoter.

T-Cell Receptor (TCR)

The T cell receptor or TCR is a molecule found on the surface of T cells that is responsible for recognizing antigens bound to major histocompatibility complex (MHC) molecules. The binding between TCR and antigen is of relatively low affinity and is degenerate: many TCR recognize the same antigen and many antigens are recognized by the same TCR.

The TCR is composed of two different protein chains, i.e. it is a heterodimer. In 95% of T cells, this consists of an alpha (α) and beta (β) chain, whereas in 5% of T cells this consists of gamma and delta (γ/δ) chains. This ratio changes during ontogeny and in diseased states.

When the TCR engages with antigenic peptide and MHC (peptide/MHC), the T lymphocyte is activated through a series of biochemical events mediated by associated enzymes, co-receptors, specialized adaptor molecules, and activated or released transcription factors.

The nucleic acid construct or vector of the present invention may comprise a nucleic acid sequence encoding a TCR α chain, a TCR β chain, a TCRγ chain or a TCR δ chain. It may, for example, comprise a nucleic acid sequence encoding a TCR α chain and a nucleic acid sequence encoding a TCR β chain; or a a nucleic acid sequence encoding a TCRγ chain or a nucleic acid sequence encoding a TCR δ chain. The two nucleic acid sequences may be joined by a sequence enabling co-expression of the two TCR chains, such as an internal promoter, an IRES sequence or a cleavage site such as a self-cleaving site.

Chimeric Antigen Receptors (CARs)

The nucleic acid sequence of interest (NOI) may encode a chimeric antigen receptor (CAR).

Classical CARs are chimeric type I trans-membrane proteins which connect an extracellular antigen-recognizing domain (binder) to an intracellular signalling domain (endodomain). The binder is typically a single-chain variable fragment (scFv) derived from a monoclonal antibody (mAb), but it can be based on other formats which comprise an antigen binding site such as a ligand. A spacer domain may be necessary to isolate the binder from the membrane and to allow it a suitable orientation. A common spacer domain used is the Fc of IgG1. More compact spacers can suffice e.g. the stalk from CD8α and even just the IgG1 hinge alone, depending on the antigen. A trans-membrane domain anchors the protein in the cell membrane and connects the spacer to the endodomain which may comprise or associate with an intracellular signalling domain.

Early CAR designs had intracellular signalling domains derived from the intracellular parts of either the γ chain of the FcεR1 or CD3ζ. Consequently, these first generation receptors transmitted immunological signal 1, which was sufficient to trigger T-cell killing of cognate target cells but failed to fully activate the T-cell to proliferate and survive. To overcome this limitation, compound signalling domains have been constructed: fusion of the intracellular part of a T-cell co-stimulatory molecule to that of CD3ζ results in second generation receptors which can transmit an activating and co-stimulatory signal simultaneously after antigen recognition. The co-stimulatory domain most commonly used is that of CD28. This supplies the most potent co-stimulatory signal—namely immunological signal 2, which triggers T-cell proliferation. Some receptors have also been described which include TNF receptor family endodomains, such as the closely related OX40 and 41BB which transmit survival signals. Even more potent third generation CARs have now been described which have intracellular signalling domains capable of transmitting activation, proliferation and survival signals.

CAR-encoding nucleic acids may be transferred to T cells using, for example, retroviral vectors. In this way, a large number of antigen-specific T cells can be generated for adoptive cell transfer. When the CAR binds the target-antigen, this results in the transmission of an activating signal to the T-cell it is expressed on. Thus the CAR directs the specificity and cytotoxicity of the T cell towards cells expressing the targeted antigen.

Vector

In a third aspect, the present invention provides a vector which comprises a nucleic acid sequence or nucleic acid construct of the invention.

The present invention also provides a vector, or kit of vectors which comprises one or more nucleic acid sequence(s) or nucleic acid construct(s) of the invention and optionally one of more additions nucleic acid sequences of interest (NOI). Such a vector may be used to introduce the nucleic acid sequence(s) or nucleic acid construct(s) into a host cell so that it expresses one or more chimeric protein(s) according to the first aspect of the invention and optionally one or more other proteins of interest (POI). The kit may also comprise a CID.

The vector may, for example, be a plasmid or a viral vector, such as a retroviral vector or a lentiviral vector, or a transposon based vector or synthetic mRNA.

The vector may be capable of transfecting or transducing a T cell.

The NOI may, for example encode a chimeric antigen receptor or a T-cell receptor, such that when the vector is used to transduce a target cell, the target cell co-expresses a chimeric protein and a chimeric antigen receptor or T-cell receptor.

Cell

The present invention also relates to a cell comprising a chimeric protein according to the first aspect of the invention.

The cell may express a chimeric protein having two heterodimerization domains, according of the first embodiment of the first aspect of the present invention.

The cell may express two chimeric proteins; one which comprises a caspase domain and a heterodimerization domain which comprises an FK506-binding protein (FKBP); and one which comprises a caspase domain and a heterodimerization domain which comprises an FRB domain of mTOR, according to the second embodiment of the first aspect of the invention.

There is also provided a cell which expresses two proteins:

Ht1-Casp and Ht2-Ht2 in which Ht1-Casp is a chimeric protein comprising a caspase domain (Casp) and a first heterodimerization domain (Ht1); and Ht2-Ht2 is an interfacing protein comprising two second heterodimerization domains (Ht2) such that, in the presence of a chemical inducer of dimerization (CID), a pair of the chimeric proteins Ht1-Casp9 interact such that Ht1 from each chimeric protein heterodimerizes with an Ht2 domain from the interfacing protein, causing homodimerization of the two caspase domains (see FIG. 1d).

The cell may, for example, be an immune cell such as a T-cell or a natural killer (NK) cell.

The cell may be a stem cell such as a haematopoietic stem cell.

T cells or T lymphocytes which are a type of lymphocyte that play a central role in cell-mediated immunity. They can be distinguished from other lymphocytes, such as B cells and natural killer cells (NK cells), by the presence of a T-cell receptor (TCR) on the cell surface. There are various types of T cell, as summarised below.

Helper T helper cells (TH cells) assist other white blood cells in immunologic processes, including maturation of B cells into plasma cells and memory B cells, and activation of cytotoxic T cells and macrophages. TH cells express CD4 on their surface. TH cells become activated when they are presented with peptide antigens by MHC class II molecules on the surface of antigen presenting cells (APCs). These cells can differentiate into one of several subtypes, including TH1, TH2, TH3, TH17, Th9, or TFH, which secrete different cytokines to facilitate different types of immune responses.

Cytolytic T cells (TC cells, or CTLs) destroy virally infected cells and tumor cells, and are also implicated in transplant rejection. CTLs express the CD8 at their surface. These cells recognize their targets by binding to antigen associated with MHC class I, which is present on the surface of all nucleated cells. Through IL-10, adenosine and other molecules secreted by regulatory T cells, the CD8+ cells can be inactivated to an anergic state, which prevent autoimmune diseases such as experimental autoimmune encephalomyelitis.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells (TCM cells) and two types of effector memory T cells (TEM cells and TEMRA cells). Memory cells may be either CD4+ or CD8+. Memory T cells typically express the cell surface protein CD45RO.

Regulatory T cells (Treg cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus.

Two major classes of CD4+ Treg cells have been described—naturally occurring Treg cells and adaptive Treg cells.

Naturally occurring Treg cells (also known as CD4+ CD25+FoxP3+ Treg cells) arise in the thymus and have been linked to interactions between developing T cells with both myeloid (CD11c+) and plasmacytoid (CD123+) dendritic cells that have been activated with TSLP. Naturally occurring Treg cells can be distinguished from other T cells by the presence of an intracellular molecule called FoxP3. Mutations of the FOXP3 gene can prevent regulatory T cell development, causing the fatal autoimmune disease IPEX.

Adaptive Treg cells (also known as Tr1 cells or Th3 cells) may originate during a normal immune response.

Natural Killer Cells (or NK cells) are a type of cytolytic cell which form part of the innate immune system. NK cells provide rapid responses to innate signals from virally infected cells in an MHC independent manner NK cells (belonging to the group of innate lymphoid cells) are defined as large granular lymphocytes (LGL) and constitute the third kind of cells differentiated from the common lymphoid progenitor generating B and T lymphocytes. NK cells are known to differentiate and mature in the bone marrow, lymph node, spleen, tonsils and thymus where they then enter into the circulation.

Stem cells are undifferentiated cells which can differentiate into specialized cells. In mammals, there are two broad types of stem cells: embryonic stem cells, which are isolated from the inner cell mass of blastocysts, and adult stem cells, which are found in various tissues. In adult organisms, stem cells and progenitor cells act as a repair system for the body, replenishing adult tissues. In a developing embryo, stem cells can differentiate into all the specialized cells—ectoderm, endoderm and mesoderm (see induced pluripotent stem cells)—but also maintain the normal turnover of regenerative organs, such as blood, skin, or intestinal tissues.

There are three known accessible sources of autologous adult stem cells in humans:

1. Bone marrow, which requires extraction by harvesting, i.e. drilling into bone.
2. Adipose tissue, which requires extraction by liposuction.
3. Blood, which requires extraction through apheresis, wherein blood is drawn from the donor and passed through a machine that extracts the stem cells and returns other portions of the blood to the donor.

Adult stem cells are frequently used in medical therapies, for example in bone marrow transplantation. Stem cells can now be artificially grown and transformed (differentiated) into specialized cell types with characteristics consistent with cells of various tissues such as muscles or nerves. Embryonic cell lines and autologous embryonic stem cells generated through Somatic-cell nuclear transfer or dedifferentiation can also be used to generate specialised cell types for cell therapy.

Hematopoietic stem cells (HSCs) are the blood cells that give rise to all the other blood cells and are derived from mesoderm. They are located in the red bone marrow, which is contained in the core of most bones.

They give rise to the myeloid (monocytes and macrophages, neutrophils, basophils, eosinophils, erythrocytes, megakaryocytes/platelets, dendritic cells), and lymphoid lineages (T-cells, B-cells, NK-cells). The hematopoietic tissue contains cells with long-term and short-term regeneration capacities and committed multipotent, oligopotent, and unipotent progenitors.

HSCs are a heterogeneous population. Three classes of stem cells exist, distinguished by their ratio of lymphoid to myeloid progeny (L/M) in blood. Myeloid-biased (My-bi) HSC have low L/M ratio (between 0 and 3), whereas lymphoid-biased (Ly-bi) HSC show a large ratio (>10). The third category consists of the balanced (Bala) HSC, whose L/M ratio is between 3 and 10. Only the myeloid-biased and balanced HSCs have durable self-renewal properties.

The chimeric protein-expressing cells of the invention may be any of the cell types mentioned above.

T or NK cells expressing one or more chimeric protein(s) according to the first aspect of the invention may either be created ex vivo either from a patient's own peripheral blood ($1^{st}$ party), or in the setting of a haematopoietic stem cell transplant from donor peripheral blood ($2^{nd}$ party), or peripheral blood from an unconnected donor ($3^{rd}$ party).

Alternatively, T or NK cells expressing one or more chimeric protein(s) according to the first aspect of the invention may be derived from ex vivo differentiation of inducible progenitor cells or embryonic progenitor cells to T cells. Alternatively, an immortalized T-cell line which retains its lytic function and could act as a therapeutic may be used.

In all these embodiments, chimeric protein(s)-expressing cells are generated by introducing DNA or RNA coding for the, or each, chimeric protein, and optionally an NOI by means such as transduction with a viral vector or transfection with DNA or RNA.

The cell of the invention may be an ex vivo T or NK cell from a subject. The T or NK cell may be from a peripheral blood mononuclear cell (PBMC) sample. T or NK cells may be activated and/or expanded prior to being transduced with nucleic acid encoding one or more chimeric protein(s) according to the first aspect of the invention, for example by treatment with an anti-CD3 monoclonal antibody.

The T or NK cell of the invention may be made by:
(i) isolation of a T or NK cell-containing sample from a subject or other sources listed above; and
(ii) transduction or transfection of the T or NK cells with one or more a nucleic acid sequence(s) according to the second aspect of the invention.

The present invention also provides a kit which comprises a T or NK cell comprising one or more chimeric protein(s) according to the first aspect of the invention and a CID.

Pharmaceutical Composition

The present invention also relates to a pharmaceutical composition containing a plurality of cells according to the fourth aspect of the invention. The pharmaceutical composition may additionally comprise a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

Methods

The invention also provides a method for making a cell according to the fourth aspect of the invention which comprises the step of transducing or transfecting a cell with a vector according to the third aspect of the invention.

The vector may, for example, be a retroviral or lentiviral vector.

The invention also provides a method for deleting a cell according to the fourth aspect of the invention, which comprises the step of exposing the cells to the CID, such as rapamycin or a rapamycin analog. The cells may be exposed to the CID in vivo or in vitro. Deletion of the cell may be caused by apoptosis induced by caspase activation, following CID-induced homodimerization of the caspase domains.

The CID may be administered in the form of a pharmaceutical composition. The pharmaceutical composition may additionally comprise a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

The invention also provides a method for preventing and/or treating an pathological immune reaction in a subject caused by administration of a cell according to the fourth aspect of the invention to the subject, which comprises the step of administering a CID, such as rapamycin or a rapamycin analog to the subject.

The pathological immune reaction may be selected from the following group: graft-versus-host disease; on-target, off-tumour toxicity; immune activation syndrome; and lymphoproliferative disorders.

The invention also provides a method for treating or preventing a disease in a subject, which comprises the step of administering a cell according to the fourth aspect of the invention to the subject. The cell may be in the form of a pharmaceutical composition as defined above.

The method may comprises the following steps:
(i) transducing or transfecting a sample of cells isolated from a subject with a vector according to the third aspect of the invention, and
(ii) administering the transduced/transfected cells to a patient.

A method for treating a disease relates to the therapeutic use of the cells of the present invention. Herein the cells may be administered to a subject having an existing disease or condition in order to lessen, reduce or improve at least one symptom associated with the disease and/or to slow down, reduce or block the progression of the disease.

The method for preventing a disease relates to the prophylactic use of the immune cells of the present invention. Herein such cells may be administered to a subject who has not yet contracted the disease and/or who is not showing any symptoms of the disease to prevent or impair the cause of the disease or to reduce or prevent development of at least one symptom associated with the disease. The subject may have a predisposition for, or be thought to be at risk of developing, the disease.

The methods for treating a disease provided by the present invention may involve monitoring the progression of the disease and monitoring any toxic activity and adjusting the dose of the CID administered to the subject to provide acceptable levels of disease progression and toxic activity.

Monitoring the progression of the disease means to assess the symptoms associated with the disease over time to determine if they are reducing/improving or increasing/worsening.

Toxic activities relate to adverse effects caused by the cells of the invention following their administration to a subject. Toxic activities may include, for example, immunological toxicity, biliary toxicity and respiratory distress syndrome.

In particular the invention provides a method for treating a disease in a subject, which comprises the following steps:
(i) administering a cell according to the fourth aspect of the invention to the subject;
(ii) monitoring the subject for the development of a pathological immune reaction; and
(iii) administering rapamycin or a rapamycin analogue to the subject if the subject shows signs of developing or having developed a pathological immune reaction.

The present invention provides a cell of the present invention for use in treating and/or preventing a disease.

The cell may, for example, be for use in haematopoietic stem cell transplantation, lymphocyte infusion or adoptive cell transfer.

The invention also relates to the use of a cell of the present invention in the manufacture of a medicament for the treatment and/or prevention of a disease.

The present invention also provides a CID agent capable inducing dimerizing a chimeric protein according to the first aspect of the invention for use in treating and/or preventing a toxic activity.

The present invention also provides a CID agent for use in activating a pair of caspase domains of chimeric proteins according to the first aspect of the invention in a cell.

The disease to be treated and/or prevented by the cells and methods of the present invention may be an infection, such as a viral infection.

The methods of the invention may also be for the control of pathogenic immune responses, for example in autoimmune diseases, allergies and graft-vs-host rejection.

Where the cells of the invention express a TCR or CAR, they may be useful for the treatment of a cancerous disease, such as bladder cancer, breast cancer, colon cancer, endometrial cancer, kidney cancer (renal cell), leukemia, lung cancer, melanoma, non-Hodgkin lymphoma, pancreatic cancer, prostate cancer and thyroid cancer.

The TCR/CAR-expressing cells of the present invention may be capable of killing target cells, such as cancer cells.

The invention also provides rapamycin or a rapamycin analogue for use in preventing or treating a pathological immune reaction caused by administration of a cell according to the fourth aspect of the invention to a subject.

The cells of the present invention may be used in any cellular therapy in which modified or unmodified cells are administered to a patient. An example of a cellular therapy is adoptive T cell transfer after CD34+ stem cell transplantation. Administering T cells after stem cell transfer helps to accelerate the reconstitution of an immune system in the patient recipient. When a matched related or unrelated donor is not available, or the disease is too aggressive for an extensive donor search, the use of an HLA haploidentical family donor may be effective. Such donors may be parents, siblings, or second-degree relatives. Such infusions may enhance immune recovery and thereby reduce virus infections and eliminate relapsing leukemia cells. However, the coexistence of alloreactive T cells in a donor stem cell graft may cause graft-versus-host disease (GvHD) in which the donor cells react against the recipient, which may progressively damage the skin, gut, liver, and other organs of the recipient.

Other examples of cell therapies include using native cells or cells genetically engineered to express a heterologous gene. These treatments are used for many disorders, including blood disorders, but these therapies may have negative side effects. In another method, immature progenitor cells that can differentiate into many types of mature cells, such as, for example, mesenchymal stromal cells, may be used to treat disorders by replacing the function of diseased cells. There present invention provides a rapid and effective mechanism to remove possible negative effects of donor cells used in cellular therapy.

The present invention provides a method of reducing the effect of graft versus host disease in a human patient following donor T cell transplantation, comprising transfecting or transducing human donor T cells in a donor cell culture with vector according to the present invention; administering the transduced or transfected donor T cells to the patient; subsequently detecting the presence or absence of graft versus host disease in the patient; and administering a chemical inducer of dimerization (CID) to a patient for whom the presence of graft versus host disease is detected. The T cells may be non-allodepleted.

The present invention provides a method of stem cell transplantation, comprising administering a haploidentical stem cell transplant to a human patient; and administering haploidentical donor T cells to the patient, wherein the T cells are transfected or transduced in a haploidentical donor cell culture with a vector according to the invention.

The cells may be non-allodepleted human donor T cells in a donor cell culture.

The present invention also provides a method of stem cell transplantation, comprising administering a haploidentical stem cell transplant to a human patient; and administering non-allodepleted haploidentical donor T cells to the patient, wherein the T cells are transfected or transduced in a haploidentical donor cell culture with vector according to the invention.

The haploidentical stem cell transplant may be a CD34+ haploididentical stem cell transplant. The human donor T cells may be haploidentical to the patient's T cells. The patient may any disease or disorder which may be alleviated by stem cell transplantation. The patient may have cancer, such as a solid tumour or cancer of the blood or bone marrow. The patient may have a blood or bone marrow disease. The patient may have sickle cell anemia or metachromatic leukodystrophy.

The donor cell culture may be prepared from a bone marrow sample or from peripheral blood. The donor cell culture may be prepared from donor peripheral blood mononuclear cells. In some embodiments, the donor T cells are allodepleted from the donor cell culture before transfection or transduction. Transduced or transfected T cells may be cultured in the presence of IL-2 before administration to the patient.

The invention will now be further described by way of Examples, which are meant to serve to assist one of ordinary skill in the art in carrying out the invention and are not intended in any way to limit the scope of the invention.

EXAMPLES

Example 1—Production of T-Cells Expressing Chimeric Proteins

T-cells were transduced with the different constructs. For the two-molecule rapCasp9 (FIG. 1a), T-cells were transduced with two vectors: one coding for FKBP12-Casp9 co-expressed with the green fluorescent protein eGFP by means of an internal ribosome entry sequence, and the other coding for FRB-Casp9 co-expressed with the blue fluorescent protein eBFP2. For the one molecule rapCasp9 (FIG. 1b), T-cells were transduced with just one vector coding for the respective rapCasp9 which are co-expressed eGFP. A construct which provided FKB12-Casp9 and FRB-FRBw was encoded in a tri-cistronic cassette whereby the FKBP12-Casp9 and FRB-FRBw were co-expressed using a FMD-2A like peptide and eGFP was co-expressed with an IRES. The T-cells were intentionally only partially transduced so within the cell culture a proportion of cells remained non-transduced to act as an internal negative control. As a further control, T-cells were transduced with a vector which codes for eGFP alone to exclude non-specific effects of Rapamycin on transduced cells.

Example 2—Testing Deletion of Chimeric Protein-Expressing Cells with Rapamycin

Figure 2:
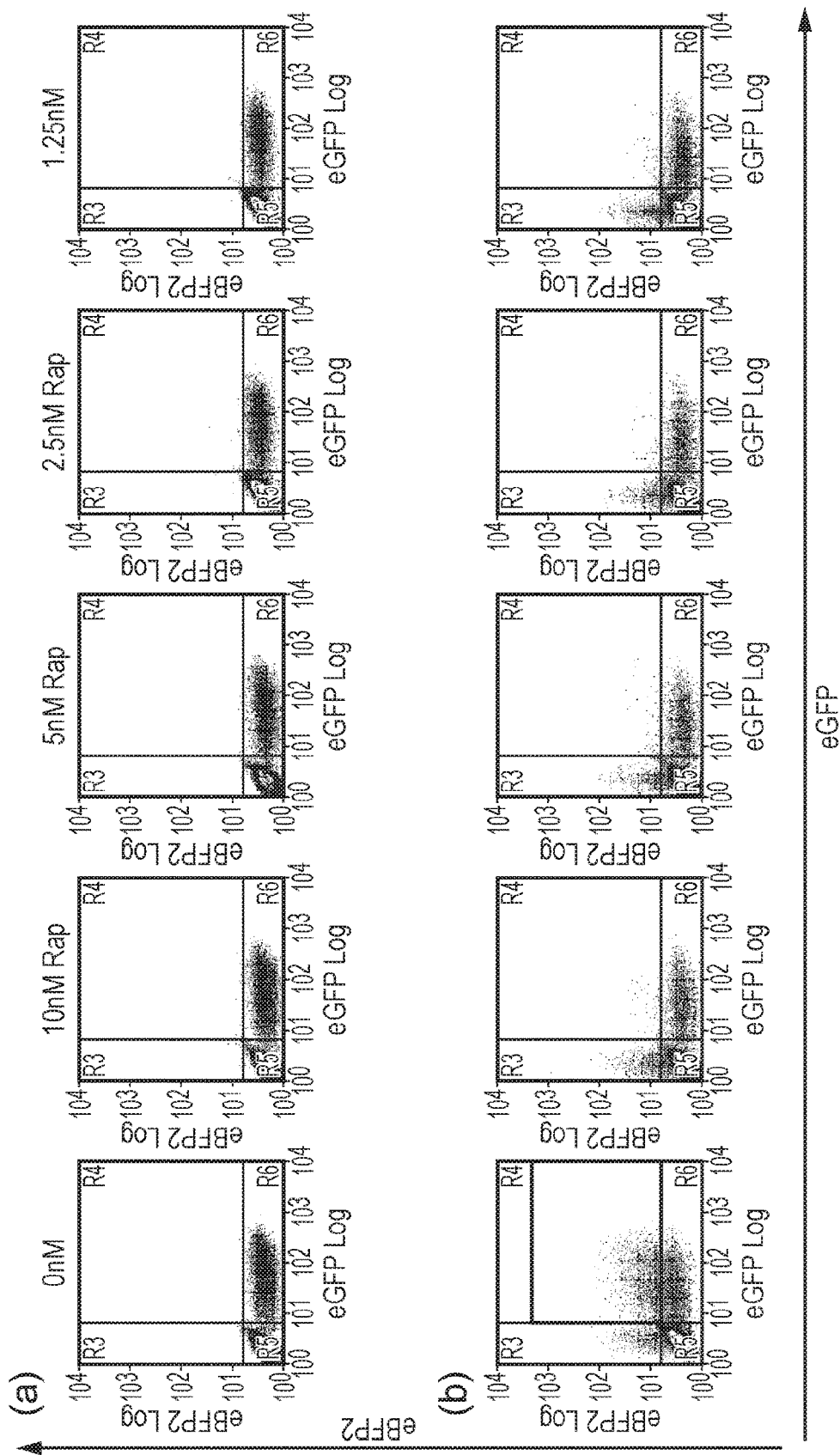
FIG. 2—Demonstration that it is possible to activate Caspase 9 with a heterodimerizer. T-cells were either transduced with eGFP alone (FIG. 2a), or co-transduced with FKBP12-dCasp9 (co-expressing eGFP) and FRB-dCasp9 (co-expressing eBFP2) (FIG. 2b). T-cells were intentionally only partially transduced so that the non-transduced T-cells would act as internal controls. T-cells were then exposed to decreasing concentrations of Rapamycin. After 48 hours, cells were stained with Annexin-V and 7AAD and analysed by flow cytometry looking at the proportion of live cells which were expressing fluorescent proteins. T-cells expressing both eGFP and eBFP2 were very effectively deleted even in the presence of the lowest concentration of Rapamycin.

T-cells were exposed to different concentrations of Rapamycin and incubated for 48 hours. Following this, T-cells were stained with Annexin-V and 7AAD and analysed by flow-cytometry. By gating on the live cells, and interrogating the population of cells expressing fluorescent proteins, survival of the transduced and non-transduced populations could be clearly measured. The dual FRB-Casp9 and FKBP12-Casp9 approach resulted in effective deletion of only double positive cells as expected. The FKBP12-FRB-Casp9 construct resulted in effective deletion of single positive cells. The FKBP12-Casp9-FRB construct resulted in minimal deletion. The FKBP12-Casp9/FRB-FRBw resulted in effective deletion of single positive cells. The control resulted in no specific deletion (FIGS. 2 and 3).

Example 3—Testing an Expanded Set of Constructs

Figure 5:
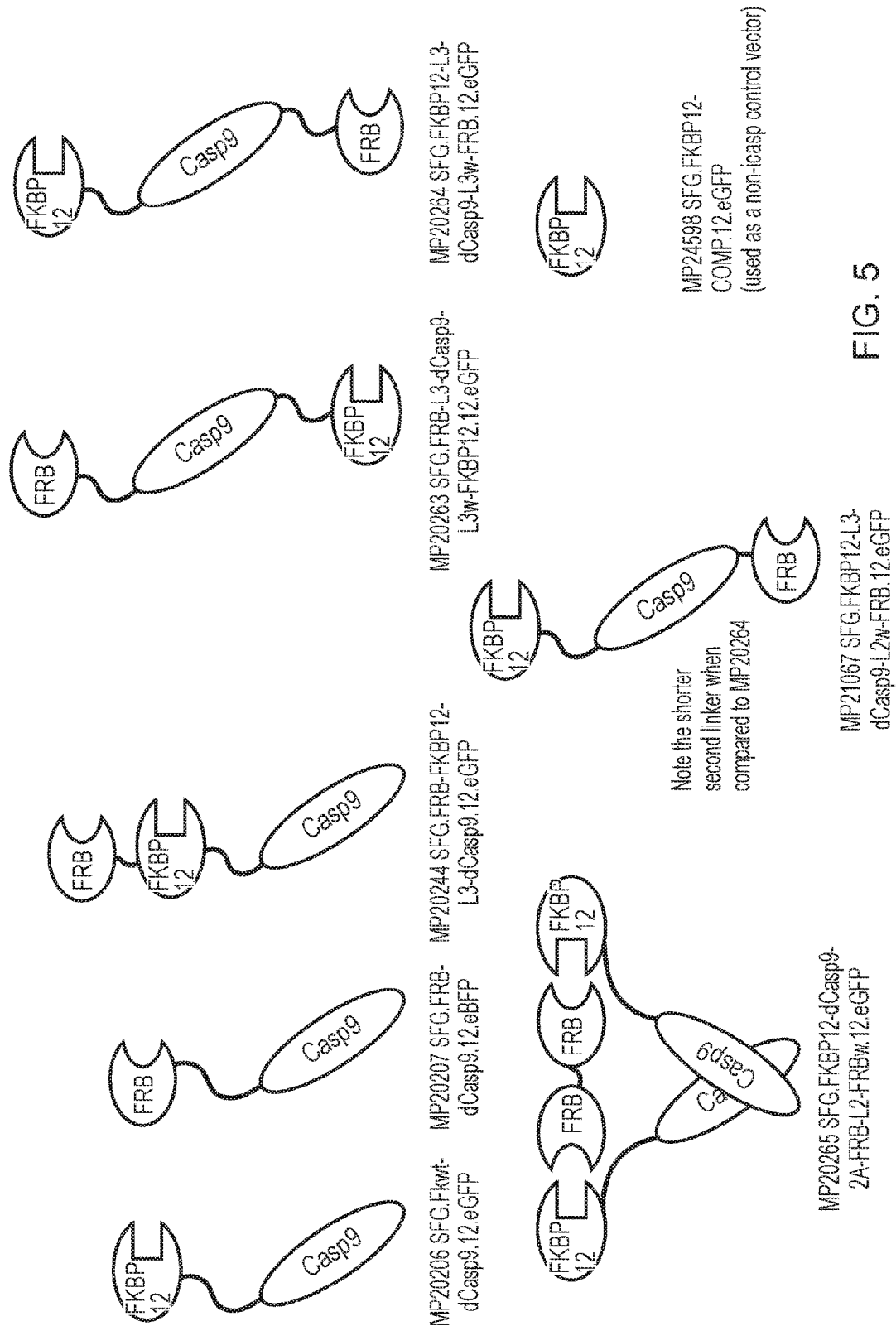
FIG. 5—Summary of the constructs tested in Example 3.
Figure 6:
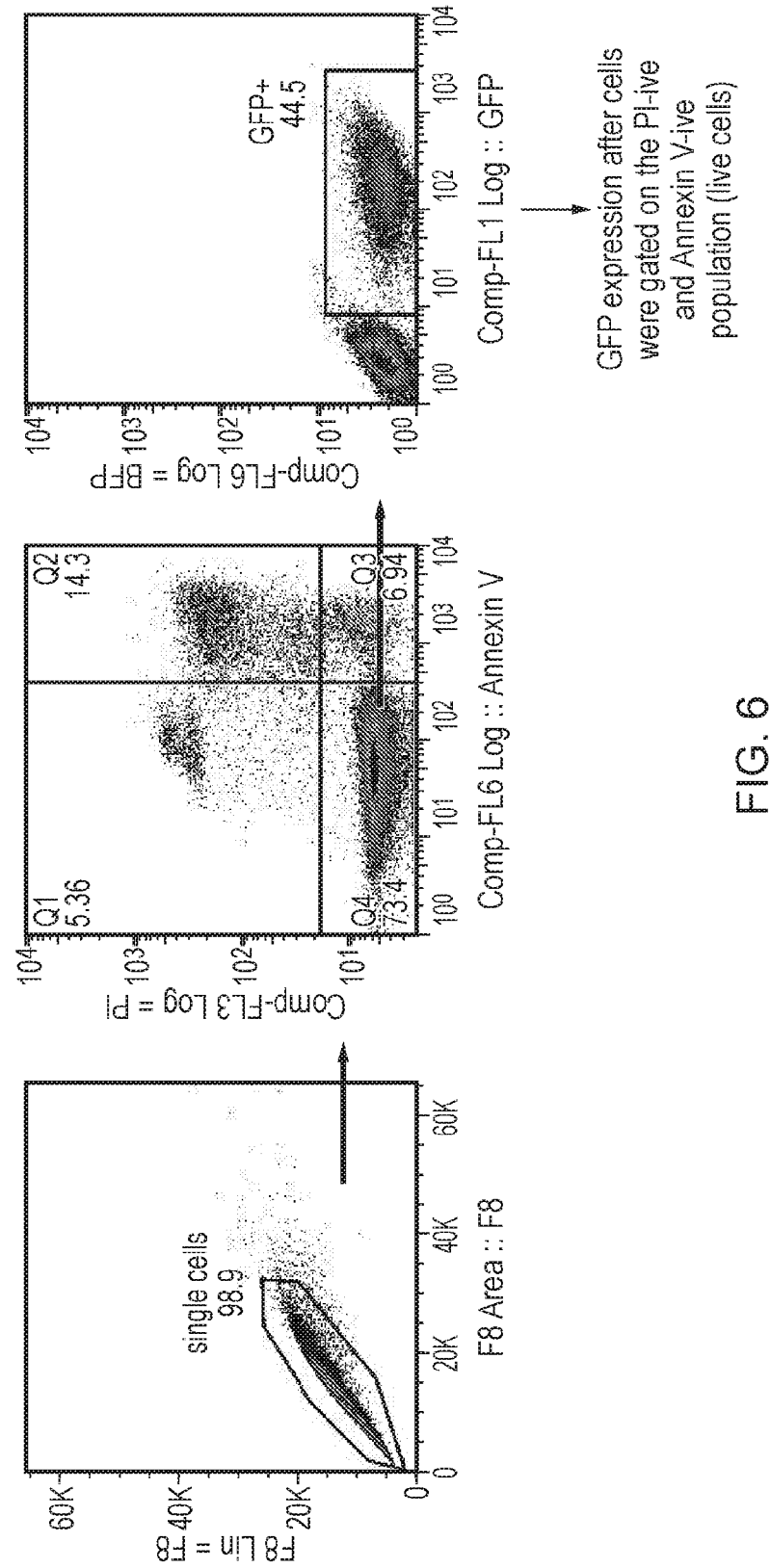
FIG. 6—Summary of gating strategy for Example 3.
Figure 7:
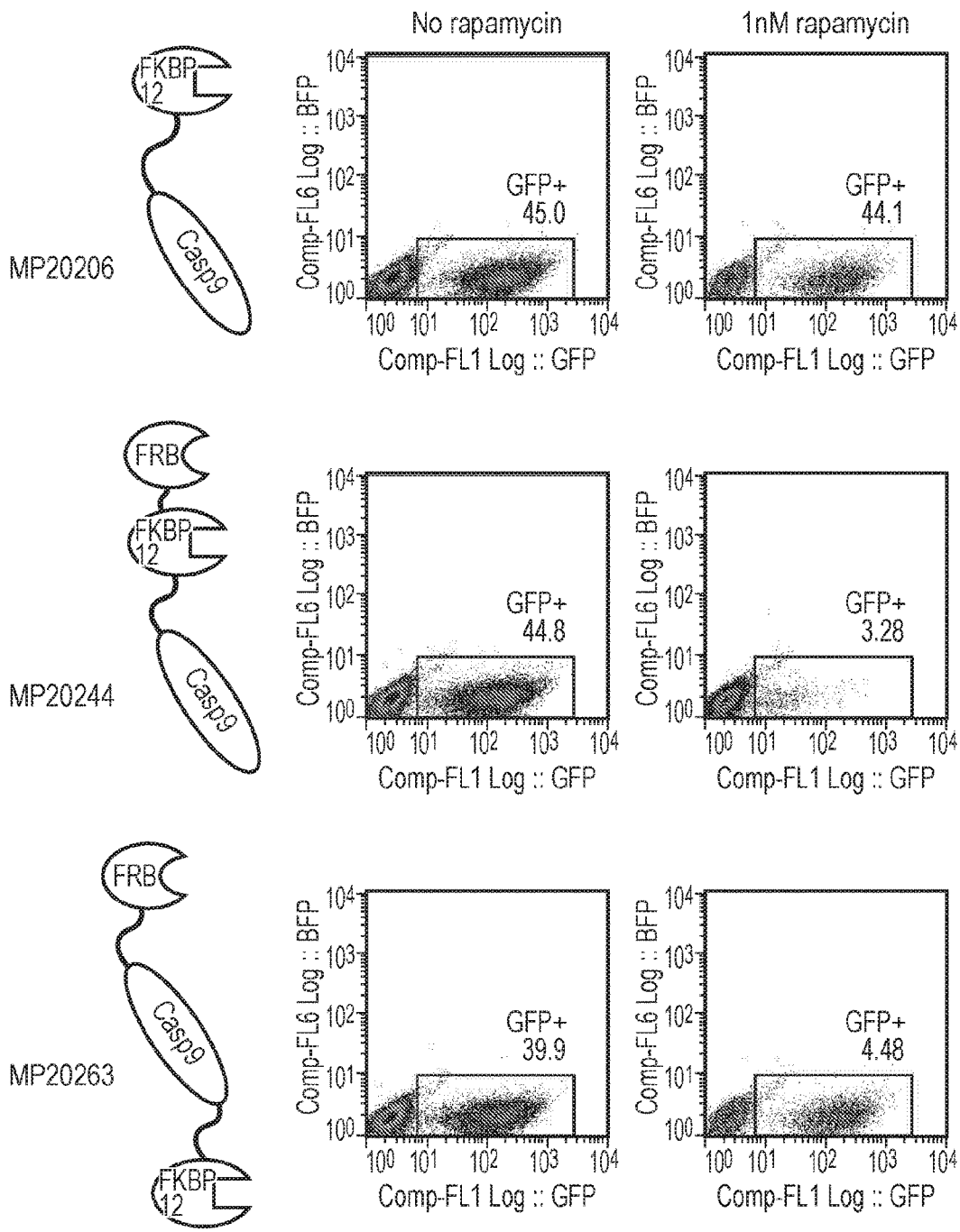
FIGS. 7, 8 and 9—Study showing the killing of Jurkat cells transfected with the constructs shown in FIG. 5 after incubation with various concentrations of rapamycin.
Figure 7:
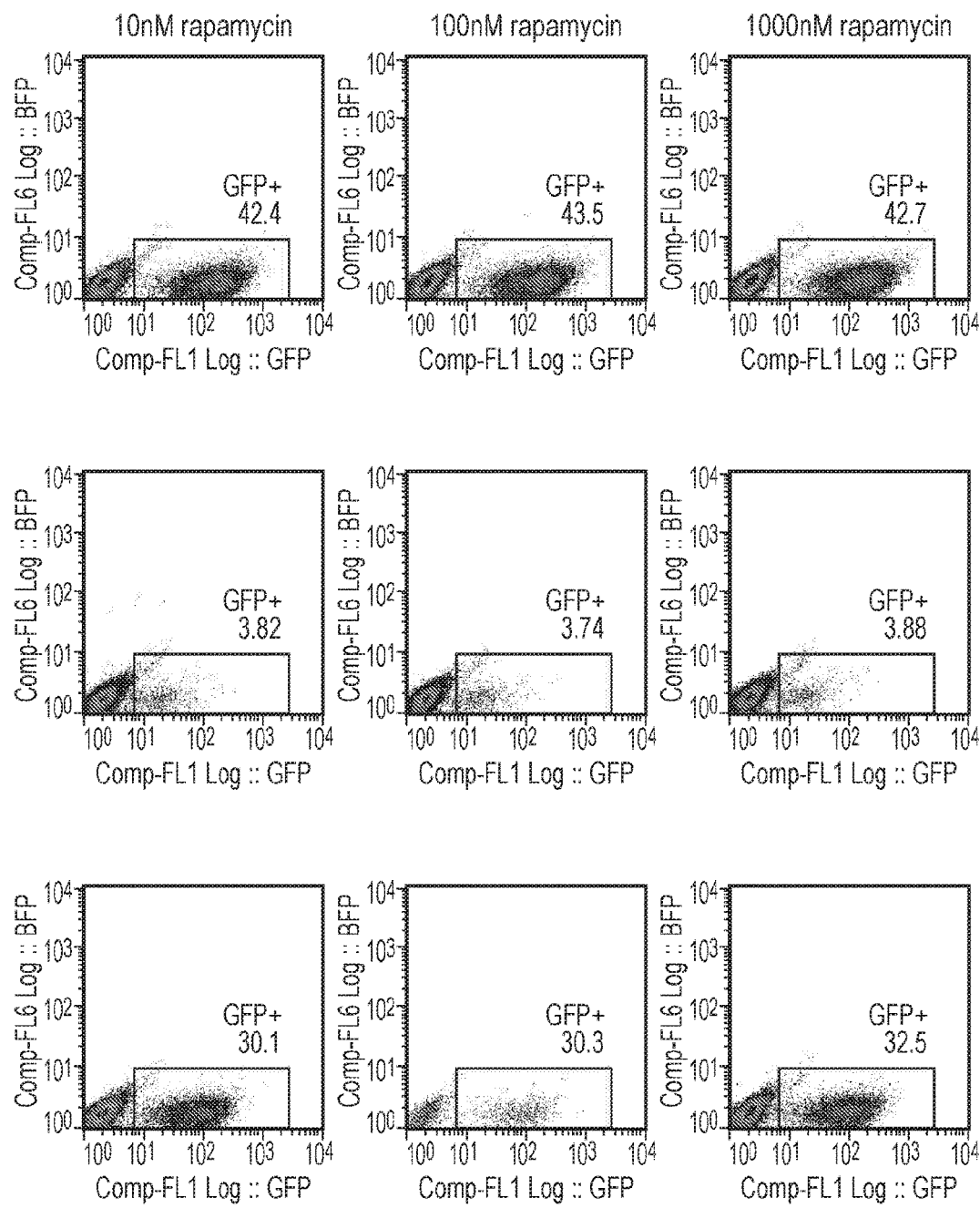
Figure 8:
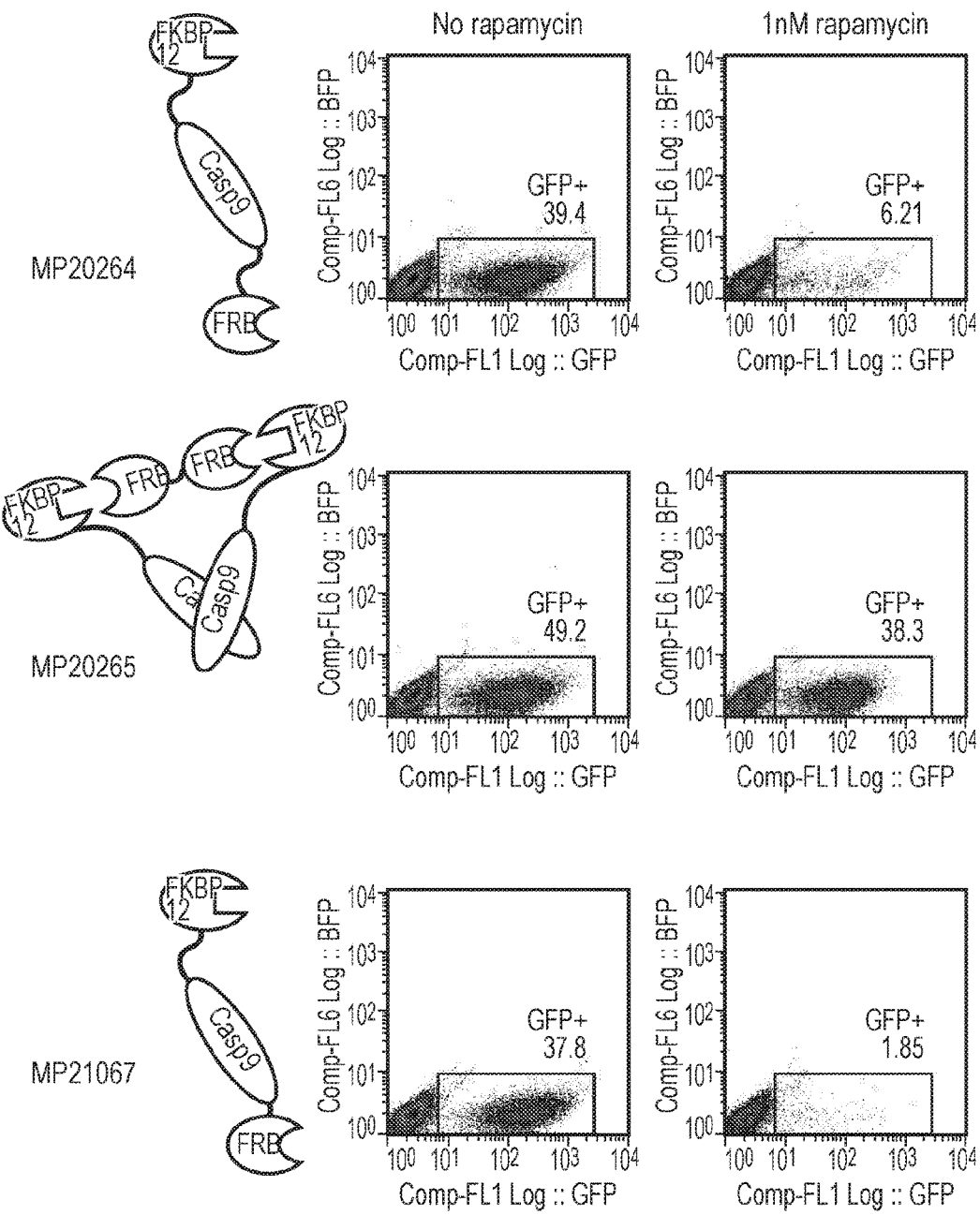
Figure 8:
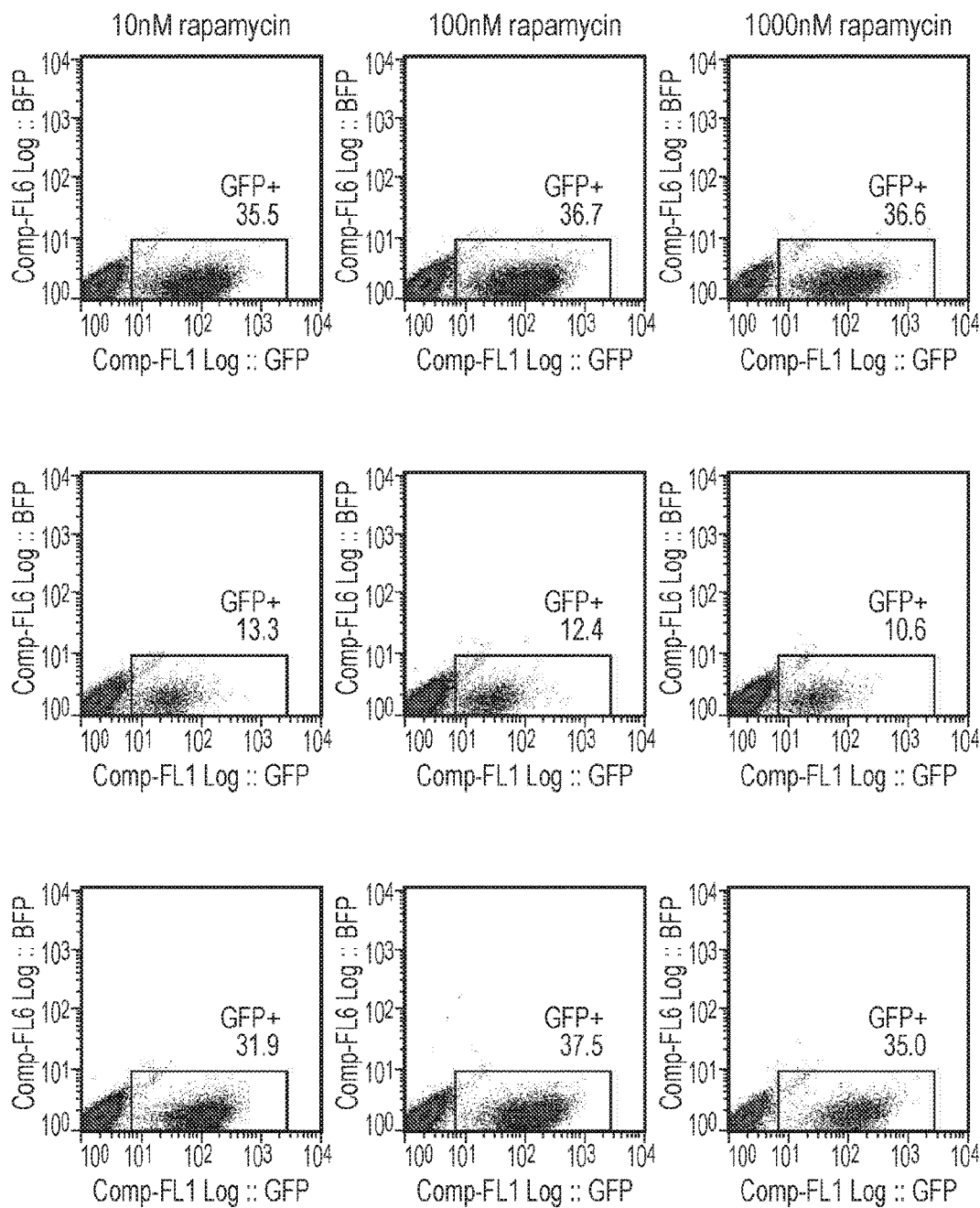
Figure 9:
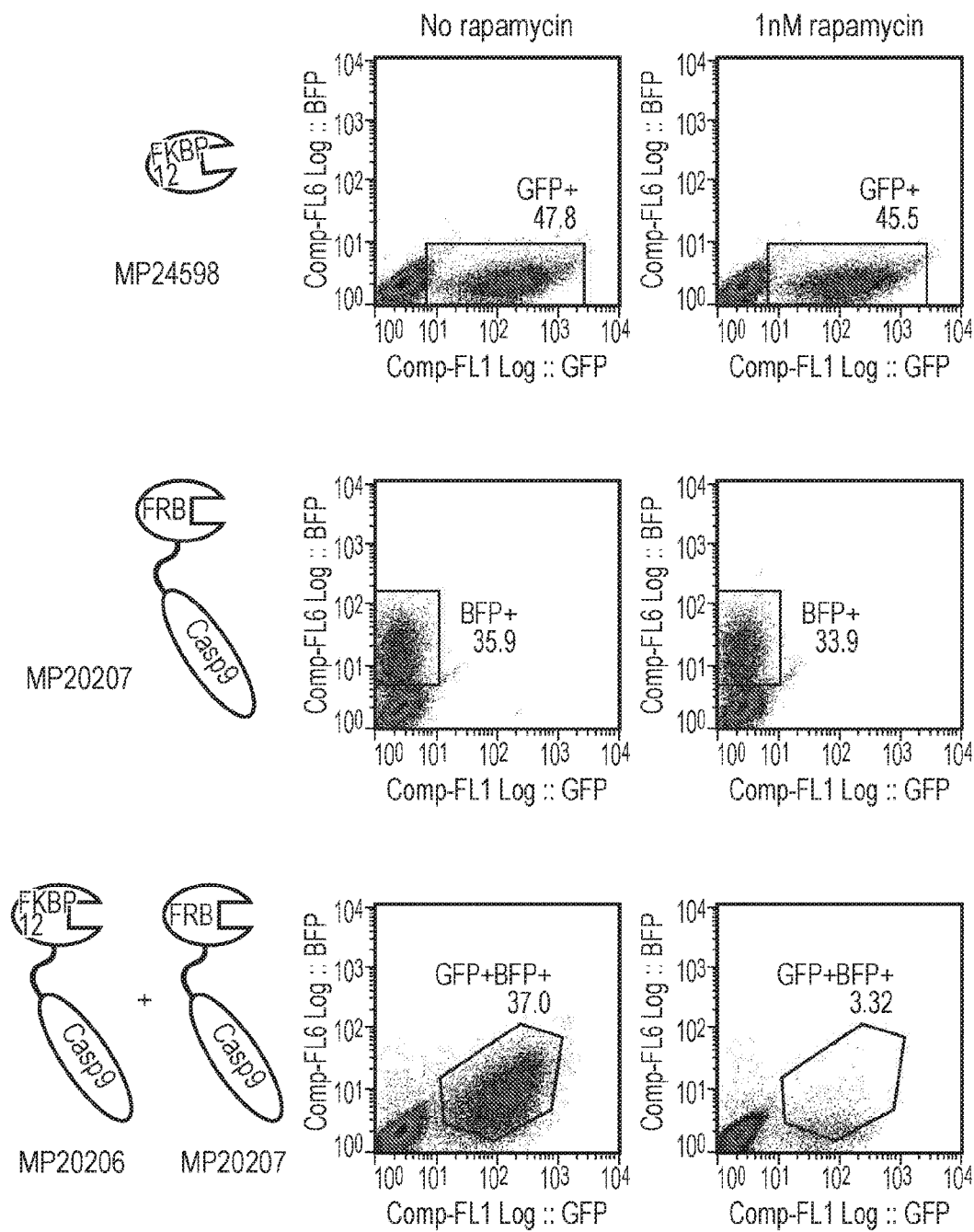
Figure 9:
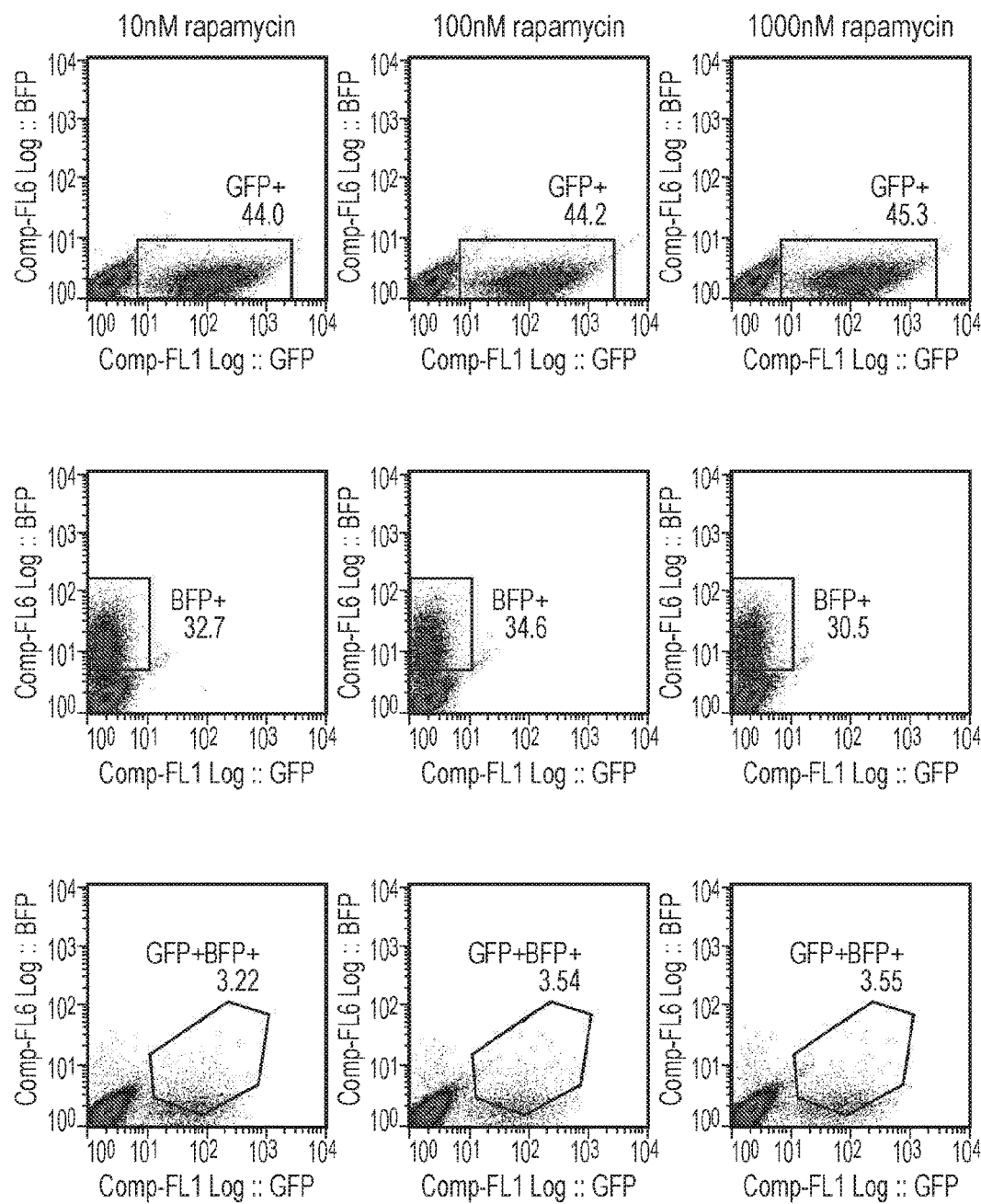
Figure 10:
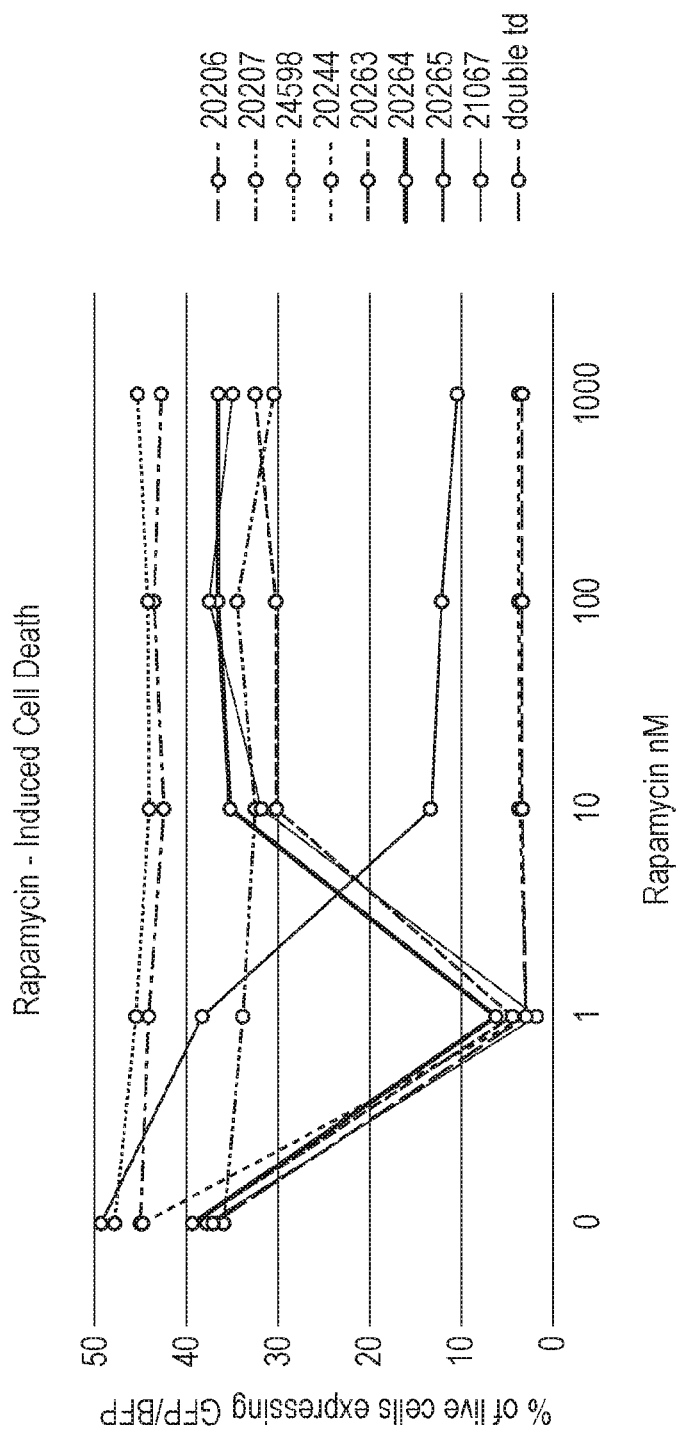
FIG. 10—Graph to summarise the FACS data shown in FIGS. 7, 8 and 9.

The constructs shown in FIG. 5 we generated and transduced into Jurkat cells. Transduced cells were mixed with non-transduced (NT) cells to have both construct positive and negative cells within the population. Rapamycin was added at a concentration of 0, 1, 10, 100 and 1000 nM and the cells were incubated for 24 h. Following harvesting, the cells were stained with PI and annexin V and analysed by FACS. The results are shown in FIGS. 6 to 9 and summarised in FIG. 10.

The construct which has a configuration as defined according to the first embodiment of the first aspect of the invention, namely MP20244, performed very well in this assay, giving very efficient killing of transfected cells at all concentrations of rapamycin above and including 1 nM.

The pair of constructs having a configuration as defined according to the second embodiment of the first aspect of the invention, namely MP20206 and MP20207 also performed very well, giving very efficient killing of transfected cells at all concentrations of rapamycin above and including 1 nM.

The construct having a configuration as defined according to the third embodiment of the first aspect of the invention, namely MP20265, also performed well, giving some killing at 1 nM rapamycin and efficient killing at concentrations of rapamycin of 10 nM and above.

Constructs having a configuration as defined according to the fourth embodiment of the first aspect of the invention, namely MP20263, MP20264 and MP21067 performed well at 1 nM rapamycin, but at higher concentrations of rapamycin killing was less efficient.

Example 4—Testing the Constructs with Temsirolimus

In an equivalent experiment to the one described in Example 3, cells expressing the constructs shown in FIG. 5 were treated with both rapamycin and temsirolimus, a rapamycin analogue.

As with the experiment outlined in Example 3, the transduced Jurkat cells were mixed with non-transduced (NT) giving a population containing both cells expressing the constructs and non-transduced cells.

Cells at a concentration of with $2 \times 10^5$ cells per well were either left untreated, or were treated with rapamycin or temsirolimus at the following concentrations: 0.01, 0.1, 1, 10 nM (of either rapamycin or temsirolimus)

Figure 11:
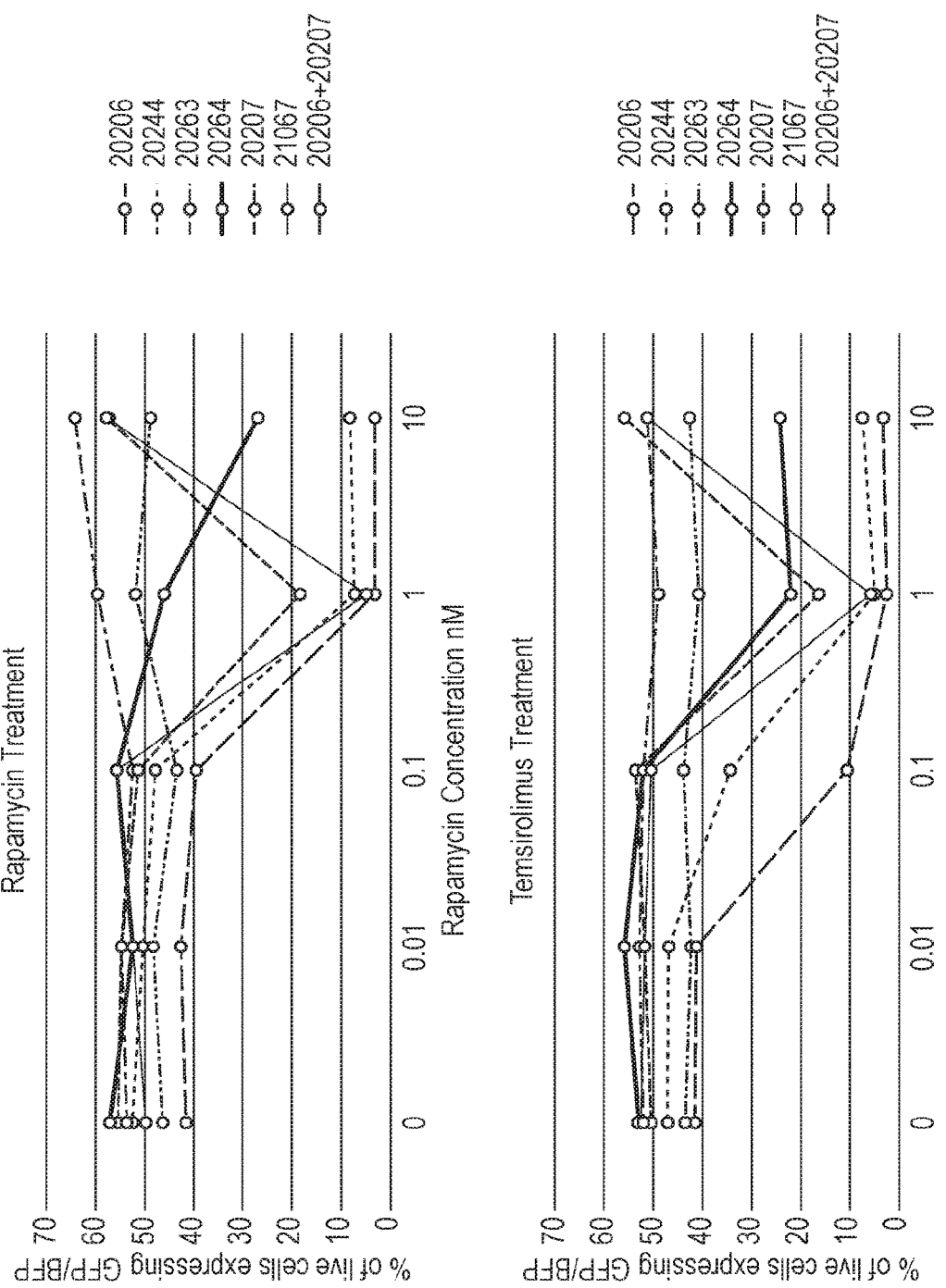
FIG. 11—Graph comparing Jurkat cell killing in the presence of rapamycin vs temsirolimus.

Cells were incubated for 24 h and were then stained for Annexin V and PI and were analysed by FACS. The results are shown in FIG. 11.

An equivalent pattern of Jurkat cell killing was observed with the various constructs shown in FIG. 5 in the presence of temsirolimus as had been previously observed in the presence of rapamycin.

In particular, the construct MP20244, which has a configuration as defined according to the first embodiment of the first aspect of the invention; and the pair of constructs MP20206 and MP20207, having a configuration as defined according to the second embodiment of the first aspect of the invention, both performed well. Both gave efficient killing of transfected cells at all concentrations of temsirolimus above and including 1 nM.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A chimeric protein having the formula:
Ht1-Ht2-Casp, wherein
Casp is a caspase domain;
Ht1 is a first heterodimerization domain; and
Ht2 is a second heterodimerization domain;
wherein one heterodimerization domain comprises an FK506-binding protein (FKBP) and the other heterodimerization domain comprises an FRB domain of mTOR;
and wherein, in the presence of rapamycin or a rapamycin analog, an identical pair of the chimeric proteins interact such that Ht1 from one chimeric protein heterodimerizes with Ht2 from the other chimeric protein, causing homodimerization of the two caspase domains.

2. The chimeric protein according to claim 1, wherein Ht1 comprises FRB and Ht2 comprises FKBP.

3. A nucleic acid comprising a nucleotide sequence which encodes a chimeric protein having the formula: Ht1-Ht2-Casp,
wherein Casp is a caspase domain; Ht1 is a first heterodimerization domain; and Ht2 is a second heterodimerization domain;
wherein one heterodimerization domain comprises an FK506-binding protein (FKBP) and the other heterodimerization domain comprises an FRB domain of mTOR.

4. The nucleic acid construct which comprises one or more nucleic acid(s) according to claim 3 and a nucleic acid that comprises a nucleotide sequence encoding a T-cell receptor (TCR) or chimeric antigen receptor (CAR).

5. A vector which comprises a nucleic acid according to claim 3.

6. A cell which expresses a chimeric protein according to claim 1.

7. The cell according to claim 6, which is a haematopoietic stem cell, a lymphocyte or a T cell.

8. A method for making a cell which expresses a chimeric protein, the method comprising the step of transducing or transfecting a cell with a vector according to claim 5.

9. A method for deleting a cell according to claim 6, which comprises the step of exposing the cells to a rapamycin or a rapamycin analog.

10. A method for preventing and/or treating a pathological immune reaction in a subject caused by administration of a cell according to claim 6 to the subject, which comprises the step of administering rapamycin or a rapamycin analog to the subject.

11. The method according to claim 10, wherein the pathological immune reaction is selected from the following group: graft-versus-host disease; on-target, off-tumour toxicity; immune activation syndrome; and lymphoproliferative disorders.

12. A vector which comprises a nucleic acid construct according to claim 4.

13. A method for making a cell which expresses a chimeric protein, the method comprising transducing or transfecting a cell with a vector according to claim 12.

* * * * *

SEQUENCE LISTING

```
<160> NUMBER OF SEQ ID NOS: 17

<210> SEQ ID NO 1
<211> LENGTH: 517
<212> TYPE: PRT
<213> ORGANISM: Artificial Sequence
<220> FEATURE:
<223> OTHER INFORMATION: Chimeric protein FRB-FKBP12-L3-dCasp9

<400> SEQUENCE: 1

Met Ala Ser Arg Ile Leu Trp His Glu Met Trp His Glu Gly Leu Glu
1               5                   10                  15

Glu Ala Ser Arg Leu Tyr Phe Gly Glu Arg Asn Val Lys Gly Met Phe
            20                  25                  30

Glu Val Leu Glu Pro Leu His Ala Met Met Glu Arg Gly Pro Gln Thr
        35                  40                  45

Leu Lys Glu Thr Ser Phe Asn Gln Ala Tyr Gly Arg Asp Leu Met Glu
    50                  55                  60

Ala Gln Glu Trp Cys Arg Lys Tyr Met Lys Ser Gly Asn Val Lys Asp
65                  70                  75                  80

Leu Leu Gln Ala Trp Asp Leu Tyr Tyr His Val Phe Arg Arg Ile Ser
                85                  90                  95

Lys Leu Glu Tyr Ser Gly Gly Gly Ser Leu Glu Gly Val Gln Val Glu
            100                 105                 110

Thr Ile Ser Pro Gly Asp Gly Arg Thr Phe Pro Lys Arg Gly Gln Thr
        115                 120                 125

Cys Val Val His Tyr Thr Gly Met Leu Glu Asp Gly Lys Lys Phe Asp
    130                 135                 140

Ser Ser Arg Asp Arg Asn Lys Pro Phe Lys Phe Met Leu Gly Lys Gln
145                 150                 155                 160

Glu Val Ile Arg Gly Trp Glu Glu Gly Val Ala Gln Met Ser Val Gly
                165                 170                 175

Gln Arg Ala Lys Leu Thr Ile Ser Pro Asp Tyr Ala Tyr Gly Ala Thr
            180                 185                 190

Gly His Pro Gly Ile Ile Pro Pro His Ala Thr Leu Val Phe Asp Val
        195                 200                 205

Glu Leu Leu Lys Leu Glu Ser Gly Gly Gly Ser Gly Gly Gly Gly
    210                 215                 220

Ser Gly Gly Gly Ser Gly Val Asp Gly Phe Gly Asp Val Gly Ala
225                 230                 235                 240

Leu Glu Ser Leu Arg Gly Asn Ala Asp Leu Ala Tyr Ile Leu Ser Met
                245                 250                 255
```

```
Glu Pro Cys Gly His Cys Leu Ile Ile Asn Asn Val Asn Phe Cys Arg
                260                 265                 270

Glu Ser Gly Leu Arg Thr Arg Thr Gly Ser Asn Ile Asp Cys Glu Lys
            275                 280                 285

Leu Arg Arg Arg Phe Ser Ser Leu His Phe Met Val Glu Val Lys Gly
290                 295                 300

Asp Leu Thr Ala Lys Lys Met Val Leu Ala Leu Leu Glu Leu Ala Gln
305                 310                 315                 320

Gln Asp His Gly Ala Leu Asp Cys Cys Val Val Ile Leu Ser His
                325                 330                 335

Gly Cys Gln Ala Ser His Leu Gln Phe Pro Gly Ala Val Tyr Gly Thr
                340                 345                 350

Asp Gly Cys Pro Val Ser Val Glu Lys Ile Val Asn Ile Phe Asn Gly
                355                 360                 365

Thr Ser Cys Pro Ser Leu Gly Gly Lys Pro Lys Leu Phe Phe Ile Gln
            370                 375                 380

Ala Cys Gly Gly Glu Gln Lys Asp His Gly Phe Glu Val Ala Ser Thr
385                 390                 395                 400

Ser Pro Glu Asp Glu Ser Pro Gly Ser Asn Pro Glu Pro Asp Ala Thr
                405                 410                 415

Pro Phe Gln Glu Gly Leu Arg Thr Phe Asp Gln Leu Asp Ala Ile Ser
                420                 425                 430

Ser Leu Pro Thr Pro Ser Asp Ile Phe Val Ser Tyr Ser Thr Phe Pro
            435                 440                 445

Gly Phe Val Ser Trp Arg Asp Pro Lys Ser Gly Ser Trp Tyr Val Glu
            450                 455                 460

Thr Leu Asp Asp Ile Phe Glu Gln Trp Ala His Ser Glu Asp Leu Gln
465                 470                 475                 480

Ser Leu Leu Leu Arg Val Ala Asn Ala Val Ser Val Lys Gly Ile Tyr
                485                 490                 495

Lys Gln Met Pro Gly Cys Phe Asn Phe Leu Arg Lys Lys Leu Phe Phe
                500                 505                 510

Lys Thr Ser Ala Ser
            515

<210> SEQ ID NO 2
<211> LENGTH: 402
<212> TYPE: PRT
<213> ORGANISM: Artificial Sequence
<220> FEATURE:
<223> OTHER INFORMATION: Chimeric protein FKBP12-dCasp9

<400> SEQUENCE: 2

Met Leu Glu Gly Val Gln Val Glu Thr Ile Ser Pro Gly Asp Gly Arg
1               5                   10                  15

Thr Phe Pro Lys Arg Gly Gln Thr Cys Val Val His Tyr Thr Gly Met
                20                  25                  30

Leu Glu Asp Gly Lys Lys Phe Asp Ser Ser Arg Asp Arg Asn Lys Pro
            35                  40                  45

Phe Lys Phe Met Leu Gly Lys Gln Glu Val Ile Arg Gly Trp Glu Glu
        50                  55                  60

Gly Val Ala Gln Met Ser Val Gly Gln Arg Ala Lys Leu Thr Ile Ser
65                  70                  75                  80

Pro Asp Tyr Ala Tyr Gly Ala Thr Gly His Pro Gly Ile Ile Pro Pro
                85                  90                  95
```

His Ala Thr Leu Val Phe Asp Val Glu Leu Leu Lys Leu Glu Ser Gly
            100                 105                 110

Gly Gly Ser Gly Val Asp Gly Phe Gly Asp Val Gly Ala Leu Glu Ser
            115                 120                 125

Leu Arg Gly Asn Ala Asp Leu Ala Tyr Ile Leu Ser Met Glu Pro Cys
130                 135                 140

Gly His Cys Leu Ile Ile Asn Asn Val Asn Phe Cys Arg Glu Ser Gly
145                 150                 155                 160

Leu Arg Thr Arg Thr Gly Ser Asn Ile Asp Cys Glu Lys Leu Arg Arg
                165                 170                 175

Arg Phe Ser Ser Leu His Phe Met Val Glu Val Lys Gly Asp Leu Thr
                180                 185                 190

Ala Lys Lys Met Val Leu Ala Leu Leu Glu Leu Ala Gln Gln Asp His
            195                 200                 205

Gly Ala Leu Asp Cys Cys Val Val Val Ile Leu Ser His Gly Cys Gln
210                 215                 220

Ala Ser His Leu Gln Phe Pro Gly Ala Val Tyr Gly Thr Asp Gly Cys
225                 230                 235                 240

Pro Val Ser Val Glu Lys Ile Val Asn Ile Phe Asn Gly Thr Ser Cys
                245                 250                 255

Pro Ser Leu Gly Gly Lys Pro Lys Leu Phe Phe Ile Gln Ala Cys Gly
            260                 265                 270

Gly Glu Gln Lys Asp His Gly Phe Glu Val Ala Ser Thr Ser Pro Glu
        275                 280                 285

Asp Glu Ser Pro Gly Ser Asn Pro Glu Pro Asp Ala Thr Pro Phe Gln
290                 295                 300

Glu Gly Leu Arg Thr Phe Asp Gln Leu Asp Ala Ile Ser Ser Leu Pro
305                 310                 315                 320

Thr Pro Ser Asp Ile Phe Val Ser Tyr Ser Thr Phe Pro Gly Phe Val
                325                 330                 335

Ser Trp Arg Asp Pro Lys Ser Gly Ser Trp Tyr Val Glu Thr Leu Asp
            340                 345                 350

Asp Ile Phe Glu Gln Trp Ala His Ser Glu Asp Leu Gln Ser Leu Leu
        355                 360                 365

Leu Arg Val Ala Asn Ala Val Ser Val Lys Gly Ile Tyr Lys Gln Met
370                 375                 380

Pro Gly Cys Phe Asn Phe Leu Arg Lys Lys Leu Phe Phe Lys Thr Ser
385                 390                 395                 400

Ala Ser

<210> SEQ ID NO 3
<211> LENGTH: 392
<212> TYPE: PRT
<213> ORGANISM: Artificial Sequence
<220> FEATURE:
<223> OTHER INFORMATION: Chimeric protein FRB-dCasp9

<400> SEQUENCE: 3

Met Ala Ser Arg Ile Leu Trp His Glu Met Trp His Glu Gly Leu Glu
1               5                   10                  15

Glu Ala Ser Arg Leu Tyr Phe Gly Glu Arg Asn Val Lys Gly Met Phe
            20                  25                  30

Glu Val Leu Glu Pro Leu His Ala Met Met Glu Arg Gly Pro Gln Thr
        35                  40                  45

```
Leu Lys Glu Thr Ser Phe Asn Gln Ala Tyr Gly Arg Asp Leu Met Glu
         50                  55                  60

Ala Gln Glu Trp Cys Arg Lys Tyr Met Lys Ser Gly Asn Val Lys Asp
 65                  70                  75                  80

Leu Leu Gln Ala Trp Asp Leu Tyr Tyr His Val Phe Arg Arg Ile Ser
                 85                  90                  95

Lys Leu Glu Tyr Ser Gly Gly Ser Gly Val Asp Gly Phe Gly Asp
                100                 105                 110

Val Gly Ala Leu Glu Ser Leu Arg Gly Asn Ala Asp Leu Ala Tyr Ile
                115                 120                 125

Leu Ser Met Glu Pro Cys Gly His Cys Leu Ile Ile Asn Asn Val Asn
        130                 135                 140

Phe Cys Arg Glu Ser Gly Leu Arg Thr Arg Thr Gly Ser Asn Ile Asp
145                 150                 155                 160

Cys Glu Lys Leu Arg Arg Arg Phe Ser Ser Leu His Phe Met Val Glu
                165                 170                 175

Val Lys Gly Asp Leu Thr Ala Lys Lys Met Val Leu Ala Leu Leu Glu
                180                 185                 190

Leu Ala Gln Gln Asp His Gly Ala Leu Asp Cys Cys Val Val Val Ile
        195                 200                 205

Leu Ser His Gly Cys Gln Ala Ser His Leu Gln Phe Pro Gly Ala Val
210                 215                 220

Tyr Gly Thr Asp Gly Cys Pro Val Ser Val Glu Lys Ile Val Asn Ile
225                 230                 235                 240

Phe Asn Gly Thr Ser Cys Pro Ser Leu Gly Gly Lys Pro Lys Leu Phe
                245                 250                 255

Phe Ile Gln Ala Cys Gly Gly Glu Gln Lys Asp His Gly Phe Glu Val
            260                 265                 270

Ala Ser Thr Ser Pro Glu Asp Glu Ser Pro Gly Ser Asn Pro Glu Pro
        275                 280                 285

Asp Ala Thr Pro Phe Gln Glu Gly Leu Arg Thr Phe Asp Gln Leu Asp
        290                 295                 300

Ala Ile Ser Ser Leu Pro Thr Pro Ser Asp Ile Phe Val Ser Tyr Ser
305                 310                 315                 320

Thr Phe Pro Gly Phe Val Ser Trp Arg Asp Pro Lys Ser Gly Ser Trp
                325                 330                 335

Tyr Val Glu Thr Leu Asp Asp Ile Phe Glu Gln Trp Ala His Ser Glu
            340                 345                 350

Asp Leu Gln Ser Leu Leu Leu Arg Val Ala Asn Ala Val Ser Val Lys
        355                 360                 365

Gly Ile Tyr Lys Gln Met Pro Gly Cys Phe Asn Phe Leu Arg Lys Lys
    370                 375                 380

Leu Phe Phe Lys Thr Ser Ala Ser
385                 390

<210> SEQ ID NO 4
<211> LENGTH: 651
<212> TYPE: PRT
<213> ORGANISM: Artificial Sequence
<220> FEATURE:
<223> OTHER INFORMATION: Chimeric protein FKBP12-dCasp9-2A-FRB-FRBw

<400> SEQUENCE: 4

Met Leu Glu Gly Val Gln Val Glu Thr Ile Ser Pro Gly Asp Gly Arg
1               5                   10                  15
```

```
Thr Phe Pro Lys Arg Gly Gln Thr Cys Val Val His Tyr Thr Gly Met
                20                  25                  30

Leu Glu Asp Gly Lys Lys Phe Asp Ser Ser Arg Asp Arg Asn Lys Pro
            35                  40                  45

Phe Lys Phe Met Leu Gly Lys Gln Glu Val Ile Arg Gly Trp Glu Glu
 50                  55                  60

Gly Val Ala Gln Met Ser Val Gly Gln Arg Ala Lys Leu Thr Ile Ser
 65                  70                  75                  80

Pro Asp Tyr Ala Tyr Gly Ala Thr Gly His Pro Gly Ile Ile Pro Pro
                 85                  90                  95

His Ala Thr Leu Val Phe Asp Val Glu Leu Leu Lys Leu Glu Ser Gly
            100                 105                 110

Gly Gly Ser Gly Val Asp Gly Phe Gly Asp Val Gly Ala Leu Glu Ser
        115                 120                 125

Leu Arg Gly Asn Ala Asp Leu Ala Tyr Ile Leu Ser Met Glu Pro Cys
130                 135                 140

Gly His Cys Leu Ile Ile Asn Asn Val Asn Phe Cys Arg Glu Ser Gly
145                 150                 155                 160

Leu Arg Thr Arg Thr Gly Ser Asn Ile Asp Cys Glu Lys Leu Arg Arg
                165                 170                 175

Arg Phe Ser Ser Leu His Phe Met Val Glu Val Lys Gly Asp Leu Thr
            180                 185                 190

Ala Lys Lys Met Val Leu Ala Leu Leu Glu Leu Ala Gln Gln Asp His
        195                 200                 205

Gly Ala Leu Asp Cys Cys Val Val Val Ile Leu Ser His Gly Cys Gln
210                 215                 220

Ala Ser His Leu Gln Phe Pro Gly Ala Val Tyr Gly Thr Asp Gly Cys
225                 230                 235                 240

Pro Val Ser Val Glu Lys Ile Val Asn Ile Phe Asn Gly Thr Ser Cys
                245                 250                 255

Pro Ser Leu Gly Gly Lys Pro Lys Leu Phe Phe Ile Gln Ala Cys Gly
            260                 265                 270

Gly Glu Gln Lys Asp His Gly Phe Glu Val Ala Ser Thr Ser Pro Glu
        275                 280                 285

Asp Glu Ser Pro Gly Ser Asn Pro Glu Pro Asp Ala Thr Pro Phe Gln
290                 295                 300

Glu Gly Leu Arg Thr Phe Asp Gln Leu Asp Ala Ile Ser Ser Leu Pro
305                 310                 315                 320

Thr Pro Ser Asp Ile Phe Val Ser Tyr Ser Thr Phe Pro Gly Phe Val
                325                 330                 335

Ser Trp Arg Asp Pro Lys Ser Gly Ser Trp Tyr Val Glu Thr Leu Asp
            340                 345                 350

Asp Ile Phe Glu Gln Trp Ala His Ser Glu Asp Leu Gln Ser Leu Leu
        355                 360                 365

Leu Arg Val Ala Asn Ala Val Ser Val Lys Gly Ile Tyr Lys Gln Met
370                 375                 380

Pro Gly Cys Phe Asn Phe Leu Arg Lys Lys Leu Phe Phe Lys Thr Ser
385                 390                 395                 400

Ala Ser Gln Cys Thr Asn Tyr Ala Leu Leu Lys Leu Ala Gly Asp Val
                405                 410                 415

Glu Ser Asn Pro Gly Pro Gly Val Gln Val Glu Thr Ile Ser Pro Gly
            420                 425                 430

Asp Gly Arg Thr Phe Pro Lys Arg Gly Gln Thr Cys Val Val His Tyr
```

```
                435                 440                 445
Thr Gly Met Leu Glu Asp Gly Lys Lys Val Asp Ser Ser Arg Asp Arg
450                 455                 460
Asn Lys Pro Phe Lys Phe Met Leu Gly Lys Gln Glu Val Ile Arg Gly
465                 470                 475                 480
Trp Glu Glu Gly Val Ala Gln Met Ser Val Gly Gln Arg Ala Lys Leu
                485                 490                 495
Thr Ile Ser Pro Asp Tyr Ala Tyr Gly Ala Thr Gly His Pro Gly Ile
500                 505                 510
Ile Pro Pro His Ala Thr Leu Val Phe Asp Val Glu Leu Leu Lys Leu
515                 520                 525
Glu Ser Gly Gly Gly Ser Gly Gly Gly Ser Met Leu Glu Gly
530                 535                 540
Val Gln Val Glu Thr Ile Ser Pro Gly Asp Gly Arg Thr Phe Pro Lys
545                 550                 555                 560
Arg Gly Gln Thr Cys Val Val His Tyr Thr Gly Met Leu Glu Asp Gly
                565                 570                 575
Lys Lys Phe Asp Ser Ser Arg Asp Arg Asn Lys Pro Phe Lys Phe Met
                580                 585                 590
Leu Gly Lys Gln Glu Val Ile Arg Gly Trp Glu Glu Gly Val Ala Gln
                595                 600                 605
Met Ser Val Gly Gln Arg Ala Lys Leu Thr Ile Ser Pro Asp Tyr Ala
                610                 615                 620
Tyr Gly Ala Thr Gly His Pro Gly Ile Ile Pro Pro His Ala Thr Leu
625                 630                 635                 640
Val Phe Asp Val Glu Leu Leu Lys Leu Glu Ser
                645                 650

<210> SEQ ID NO 5
<211> LENGTH: 416
<212> TYPE: PRT
<213> ORGANISM: Homo sapiens

<400> SEQUENCE: 5

Met Asp Glu Ala Asp Arg Arg Leu Leu Arg Arg Cys Arg Leu Arg Leu
1               5                   10                  15
Val Glu Glu Leu Gln Val Asp Gln Leu Trp Asp Ala Leu Leu Ser Ser
                20                  25                  30
Glu Leu Phe Arg Pro His Met Ile Glu Asp Ile Gln Arg Ala Gly Ser
            35                  40                  45
Gly Ser Arg Arg Asp Gln Ala Arg Gln Leu Ile Ile Asp Leu Glu Thr
        50                  55                  60
Arg Gly Ser Gln Ala Leu Pro Leu Phe Ile Ser Cys Leu Glu Asp Thr
65                  70                  75                  80
Gly Gln Asp Met Leu Ala Ser Phe Leu Arg Thr Asn Arg Gln Ala Ala
                85                  90                  95
Lys Leu Ser Lys Pro Thr Leu Glu Asn Leu Thr Pro Val Val Leu Arg
                100                 105                 110
Pro Glu Ile Arg Lys Pro Glu Val Leu Arg Pro Glu Thr Pro Arg Pro
                115                 120                 125
Val Asp Ile Gly Ser Gly Gly Phe Gly Asp Val Gly Ala Leu Glu Ser
            130                 135                 140
Leu Arg Gly Asn Ala Asp Leu Ala Tyr Ile Leu Ser Met Glu Pro Cys
145                 150                 155                 160
```

Gly His Cys Leu Ile Ile Asn Asn Val Asn Phe Cys Arg Glu Ser Gly
                165                 170                 175

Leu Arg Thr Arg Thr Gly Ser Asn Ile Asp Cys Glu Lys Leu Arg Arg
            180                 185                 190

Arg Phe Ser Ser Pro His Phe Met Val Glu Val Lys Gly Asp Leu Thr
        195                 200                 205

Ala Lys Lys Met Val Leu Ala Leu Leu Glu Leu Ala Gln Gln Asp His
210                 215                 220

Gly Ala Leu Asp Cys Cys Val Val Val Ile Leu Ser His Gly Cys Gln
225                 230                 235                 240

Ala Ser His Leu Gln Phe Pro Gly Ala Val Tyr Gly Thr Asp Gly Cys
                245                 250                 255

Pro Val Ser Val Glu Lys Ile Val Asn Ile Phe Asn Gly Thr Ser Cys
            260                 265                 270

Pro Ser Leu Gly Gly Lys Pro Lys Leu Phe Phe Ile Gln Ala Cys Gly
        275                 280                 285

Gly Glu Gln Lys Asp His Gly Phe Glu Val Ala Ser Thr Ser Pro Glu
    290                 295                 300

Asp Glu Ser Pro Gly Ser Asn Pro Glu Pro Asp Ala Thr Pro Phe Gln
305                 310                 315                 320

Glu Gly Leu Arg Thr Phe Asp Gln Leu Asp Ala Ile Ser Ser Leu Pro
                325                 330                 335

Thr Pro Ser Asp Ile Phe Val Ser Tyr Ser Thr Phe Pro Gly Phe Val
            340                 345                 350

Ser Trp Arg Asp Pro Lys Ser Gly Ser Trp Tyr Val Glu Thr Leu Asp
        355                 360                 365

Asp Ile Phe Glu Gln Trp Ala His Ser Glu Asp Leu Gln Ser Leu Leu
370                 375                 380

Leu Arg Val Ala Asn Ala Val Ser Val Lys Gly Ile Tyr Lys Gln Met
385                 390                 395                 400

Pro Gly Cys Phe Asn Phe Leu Arg Lys Lys Leu Phe Phe Lys Thr Ser
                405                 410                 415

<210> SEQ ID NO 6
<211> LENGTH: 282
<212> TYPE: PRT
<213> ORGANISM: Homo sapiens

<400> SEQUENCE: 6

Gly Phe Gly Asp Val Gly Ala Leu Glu Ser Leu Arg Gly Asn Ala Asp
1               5                   10                  15

Leu Ala Tyr Ile Leu Ser Met Glu Pro Cys Gly His Cys Leu Ile Ile
                20                  25                  30

Asn Asn Val Asn Phe Cys Arg Glu Ser Gly Leu Arg Thr Arg Thr Gly
            35                  40                  45

Ser Asn Ile Asp Cys Glu Lys Leu Arg Arg Arg Phe Ser Ser Leu His
        50                  55                  60

Phe Met Val Glu Val Lys Gly Asp Leu Thr Ala Lys Lys Met Val Leu
65                  70                  75                  80

Ala Leu Leu Glu Leu Ala Gln Gln Asp His Gly Ala Leu Asp Cys Cys
                85                  90                  95

Val Val Val Ile Leu Ser His Gly Cys Gln Ala Ser His Leu Gln Phe
            100                 105                 110

Pro Gly Ala Val Tyr Gly Thr Asp Gly Cys Pro Val Ser Val Glu Lys
        115                 120                 125

-continued

```
Ile Val Asn Ile Phe Asn Gly Thr Ser Cys Pro Ser Leu Gly Gly Lys
130                 135                 140

Pro Lys Leu Phe Phe Ile Gln Ala Cys Gly Gly Glu Gln Lys Asp His
145                 150                 155                 160

Gly Phe Glu Val Ala Ser Thr Ser Pro Glu Asp Glu Ser Pro Gly Ser
                165                 170                 175

Asn Pro Glu Pro Asp Ala Thr Pro Phe Gln Glu Gly Leu Arg Thr Phe
            180                 185                 190

Asp Gln Leu Asp Ala Ile Ser Ser Leu Pro Thr Pro Ser Asp Ile Phe
        195                 200                 205

Val Ser Tyr Ser Thr Phe Pro Gly Phe Val Ser Trp Arg Asp Pro Lys
    210                 215                 220

Ser Gly Ser Trp Tyr Val Glu Thr Leu Asp Asp Ile Phe Glu Gln Trp
225                 230                 235                 240

Ala His Ser Glu Asp Leu Gln Ser Leu Leu Leu Arg Val Ala Asn Ala
                245                 250                 255

Val Ser Val Lys Gly Ile Tyr Lys Gln Met Pro Gly Cys Phe Asn Phe
            260                 265                 270

Leu Arg Lys Lys Leu Phe Phe Lys Thr Ser
        275                 280
```

<210> SEQ ID NO 7
<211> LENGTH: 108
<212> TYPE: PRT
<213> ORGANISM: Artificial Sequence
<220> FEATURE:
<223> OTHER INFORMATION: FKBP12 domain

<400> SEQUENCE: 7

```
Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
                20                  25                  30

Asp Gly Lys Lys Phe Asp Ser Ser Arg Asp Arg Asn Lys Pro Phe Lys
            35                  40                  45

Phe Met Leu Gly Lys Gln Glu Val Ile Arg Gly Trp Glu Glu Gly Val
        50                  55                  60

Ala Gln Met Ser Val Gly Gln Arg Ala Lys Leu Thr Ile Ser Pro Asp
65                  70                  75                  80

Tyr Ala Tyr Gly Ala Thr Gly His Pro Gly Ile Ile Pro Pro His Ala
                85                  90                  95

Thr Leu Val Phe Asp Val Glu Leu Leu Lys Leu Glu
            100                 105
```

<210> SEQ ID NO 8
<211> LENGTH: 100
<212> TYPE: PRT
<213> ORGANISM: Artificial Sequence
<220> FEATURE:
<223> OTHER INFORMATION: wild-type FRB segment of mTOR

<400> SEQUENCE: 8

```
Met Ala Ser Arg Ile Leu Trp His Glu Met Trp His Glu Gly Leu Glu
1               5                   10                  15

Glu Ala Ser Arg Leu Tyr Phe Gly Glu Arg Asn Val Lys Gly Met Phe
                20                  25                  30

Glu Val Leu Glu Pro Leu His Ala Met Met Glu Arg Gly Pro Gln Thr
```

```
                    35                  40                  45
Leu Lys Glu Thr Ser Phe Asn Gln Ala Tyr Gly Arg Asp Leu Met Glu
         50                   55                  60

Ala Gln Glu Trp Cys Arg Lys Tyr Met Lys Ser Gly Asn Val Lys Asp
 65                  70                  75                  80

Leu Thr Gln Ala Trp Asp Leu Tyr Tyr His Val Phe Arg Arg Ile Ser
                     85                  90                  95

Lys Leu Glu Ser
            100
```

<210> SEQ ID NO 9
<211> LENGTH: 100
<212> TYPE: PRT
<213> ORGANISM: Artificial Sequence
<220> FEATURE:
<223> OTHER INFORMATION: FRB with T to L substitution at 2098 which
      allows binding to AP21967

<400> SEQUENCE: 9

```
Met Ala Ser Arg Ile Leu Trp His Glu Met Trp His Glu Gly Leu Glu
 1               5                  10                  15

Glu Ala Ser Arg Leu Tyr Phe Gly Glu Arg Asn Val Lys Gly Met Phe
             20                  25                  30

Glu Val Leu Glu Pro Leu His Ala Met Met Glu Arg Gly Pro Gln Thr
         35                  40                  45

Leu Lys Glu Thr Ser Phe Asn Gln Ala Tyr Gly Arg Asp Leu Met Glu
     50                  55                  60

Ala Gln Glu Trp Cys Arg Lys Tyr Met Lys Ser Gly Asn Val Lys Asp
 65                  70                  75                  80

Leu Leu Gln Ala Trp Asp Leu Tyr Tyr His Val Phe Arg Arg Ile Ser
                     85                  90                  95

Lys Leu Glu Ser
            100
```

<210> SEQ ID NO 10
<211> LENGTH: 100
<212> TYPE: PRT
<213> ORGANISM: Artificial Sequence
<220> FEATURE:
<223> OTHER INFORMATION: FRB segment of mTOR with T to H substitution at
      2098 and to W at F at residue 2101 of the full mTOR

<400> SEQUENCE: 10

```
Met Ala Ser Arg Ile Leu Trp His Glu Met Trp His Glu Gly Leu Glu
 1               5                  10                  15

Glu Ala Ser Arg Leu Tyr Phe Gly Glu Arg Asn Val Lys Gly Met Phe
             20                  25                  30

Glu Val Leu Glu Pro Leu His Ala Met Met Glu Arg Gly Pro Gln Thr
         35                  40                  45

Leu Lys Glu Thr Ser Phe Asn Gln Ala Tyr Gly Arg Asp Leu Met Glu
     50                  55                  60

Ala Gln Glu Trp Cys Arg Lys Tyr Met Lys Ser Gly Asn Val Lys Asp
 65                  70                  75                  80

Leu His Gln Ala Phe Asp Leu Tyr Tyr His Val Phe Arg Arg Ile Ser
                     85                  90                  95

Lys Leu Glu Ser
            100
```

<210> SEQ ID NO 11
<211> LENGTH: 100
<212> TYPE: PRT
<213> ORGANISM: Artificial Sequence
<220> FEATURE:
<223> OTHER INFORMATION: FRB segment of mTOR with K to P substitution at residue 2095 of the full mTOR

<400> SEQUENCE: 11

```
Met Ala Ser Arg Ile Leu Trp His Glu Met Trp His Glu Gly Leu Glu
1               5                   10                  15

Glu Ala Ser Arg Leu Tyr Phe Gly Glu Arg Asn Val Lys Gly Met Phe
            20                  25                  30

Glu Val Leu Glu Pro Leu His Ala Met Met Glu Arg Gly Pro Gln Thr
        35                  40                  45

Leu Lys Glu Thr Ser Phe Asn Gln Ala Tyr Gly Arg Asp Leu Met Glu
    50                  55                  60

Ala Gln Glu Trp Cys Arg Lys Tyr Met Lys Ser Gly Asn Val Pro Asp
65                  70                  75                  80

Leu Thr Gln Ala Trp Asp Leu Tyr Tyr His Val Phe Arg Arg Ile Ser
                85                  90                  95

Lys Leu Glu Ser
            100
```

<210> SEQ ID NO 12
<211> LENGTH: 1554
<212> TYPE: DNA
<213> ORGANISM: Artificial Sequence
<220> FEATURE:
<223> OTHER INFORMATION: FRB-FKBP12-L3-Casp9 nucleotide sequence

<400> SEQUENCE: 12

```
atggcttcta gaatcctctg gcatgagatg tggcatgaag gcctggaaga ggcatctcgt      60
ttgtactttg gggaaaggaa cgtgaaaggc atgtttgagg tgctggagcc cttgcatgct     120
atgatggaac ggggccccca gactctgaag gaaacatcct taatcaggc ctatggtcga      180
gatttaatgg aggcccaaga gtggtgcagg aagtacatga atcaggaa tgtcaaggac       240
ctcctccaag cctgggacct ctattatcat gtgttccgac gaatctcaaa gctcgagtat     300
agcggcggcg gcagcctgga gggcgtgcag gtggagacca tcagcccagg cgacggcaga     360
accttccccc agagaggcca gacctgcgtg gtgcactata ccggcatgct ggaggacggc     420
aagaagttcg acagcagccg cgaccgcaat aagccctca gttcatgct gggcaagcag       480
gaggtgatca gaggctggga ggagggcgtg gcccagatga gcgtgggcca gagagccaag     540
ctgaccatca gccccgacta cgcctatggc gccaccggcc accccggcat catcccaccc     600
cacgccaccc tggtgtttga tgtggagctg ctgaagctgg agtccggcgg aggcgggtct     660
ggaggaggcg gcagcggcgg cggcgggtca ggcgtggatg gcttcggcga cgtgggagcc     720
ctggagagcc tgagaggcaa cgccgatctg gcctacatcc tgagcatgga gccctgtggc     780
cactgcctga tcatcaacaa cgtgaacttc tgccgggaga cggcctgcg gacccggacc      840
ggcagcaaca tcgactgcga gaagctgagg aggcgcttct cctccctgca ctttatggtg     900
gaggtgaaag gcgatctgac tgccaagaaa atggtgctgg ccctgctgga gctggccag      960
caggaccacg gagccctgga ttgctgtgtg gtggtgatcc tgtcccacgg ctgccaggcc    1020
agccacctgc agttccccgg agccgtgtac ggcaccgacg gctgtcccgt gtccgtggag    1080
aagatcgtga acatcttcaa cggcacctcc tgcccctccc tgggcggcaa gcccaagctg    1140
```

| ttctttatcc aggcctgtgg cggcgagcag aaggaccacg gctttgaggt ggccagcacc | 1200 |
| tcccccgagg acgagagccc aggcagcaac cccgagcccg acgccacccc cttccaggag | 1260 |
| ggcctgcgca ccttcgacca gctggacgcc atcagcagcc tgcccacccc cagcgacatc | 1320 |
| ttcgtgagct acagcacctt ccccggcttc gtgagctggc gcgatcccaa gtccggctct | 1380 |
| tggtatgtgg agaccctgga cgacatcttt gagcagtggg ctcatagcga ggacctgcag | 1440 |
| agcctgctgc tgcgcgtggc caatgccgtg agcgtgaagg catctacaa gcagatgcca | 1500 |
| ggctgcttca acttcctgcg aagaagctg ttcttcaaga ccagcgcctc ctga | 1554 |

```
<210> SEQ ID NO 13
<211> LENGTH: 1209
<212> TYPE: DNA
<213> ORGANISM: Artificial Sequence
<220> FEATURE:
<223> OTHER INFORMATION: FKBP12-dCasp9 nucleotide sequence

<400> SEQUENCE: 13
```

| atgctggagg gcgtgcaggt ggagaccatc agcccaggcg acggcagaac cttccccaag | 60 |
| agaggccaga cctgcgtggt gcactatacc ggcatgctgg aggacggcaa gaagttcgac | 120 |
| agcagccgcg accgcaataa gcccttcaag ttcatgctgg gcaagcagga ggtgatcaga | 180 |
| ggctggagg agggcgtggc ccagatgagc gtgggccaga gagccaagct gaccatcagc | 240 |
| cccgactacg cctatggcgc caccggccac cccggcatca tcccacccca cgccaccctg | 300 |
| gtgtttgatg tggagctgct gaagctggag tccggaggcg gctccggcgt ggatggcttc | 360 |
| ggcgacgtgg gagccctgga gagcctgaga ggcaacgccg atctggccta catcctgagc | 420 |
| atggagccct gtggccactg cctgatcatc aacaacgtga acttctgccg ggagagcggc | 480 |
| ctgcggaccc ggaccggcag caacatcgac tgcgagaagc tgaggaggcg cttctcctcc | 540 |
| ctgcacttta tggtggaggt gaaaggcgat ctgactgcca agaaaatggt gctggccctg | 600 |
| ctggagctgg cccagcagga ccacggagcc ctggattgct gtgtggtggt gatcctgtcc | 660 |
| cacggctgcc aggccagcca cctgcagttc cccggagccg tgtacggcac cgacggctgt | 720 |
| cccgtgtccg tggagaagat cgtgaacatc ttcaacggca cctcctgccc ctccctgggc | 780 |
| ggcaagccca gctgttctt tatccaggcc tgtggcggcg agcagaagga ccacggcttt | 840 |
| gaggtggcca cacctcccc cgaggacgag agcccaggca gcaaccccga gcccgacgcc | 900 |
| acccccttcc aggagggcct gcgcaccttc gaccagctgg acgccatcag cagcctgccc | 960 |
| acccccagcg acatcttcgt gagctacagc acctttcccg gcttcgtgag ctggcgcgat | 1020 |
| cccaagtccg gctcttggta tgtggagacc ctggacgaca tctttgagca gtgggctcat | 1080 |
| agcgaggacc tgcagagcct gctgctgcgc gtggccaatg ccgtgagcgt gaagggcatc | 1140 |
| tacaagcaga tgccaggctg cttcaacttc ctgcggaaga agctgttctt caagaccagc | 1200 |
| gcctcctga | 1209 |

```
<210> SEQ ID NO 14
<211> LENGTH: 1179
<212> TYPE: DNA
<213> ORGANISM: Artificial Sequence
<220> FEATURE:
<223> OTHER INFORMATION: FRB-dCasp9 nucleotide sequence

<400> SEQUENCE: 14
```

| atggcttcta gaatcctctg gcatgagatg tggcatgaag gcctggaaga ggcatctcgt | 60 |
| ttgtactttg gggaaaggaa cgtgaaaggc atgtttgagg tgctggagcc cttgcatgct | 120 |

```
atgatggaac ggggccccca gactctgaag gaaacatcct ttaatcaggc ctatggtcga      180
gatttaatgg aggcccaaga gtggtgcagg aagtacatga aatcagggaa tgtcaaggac      240
ctcctccaag cctgggacct ctattatcat gtgttccgac gaatctcaaa gctcgagtat      300
agcggcggcg gcagcggcgt ggatggcttc ggcgacgtgg gagccctgga gagcctgaga      360
ggcaacgccg atctggccta catcctgagc atggagccct gtggccactg cctgatcatc      420
aacaacgtga acttctgccg ggagagcggc ctgcggaccc ggaccggcag caacatcgac      480
tgcgagaagc tgaggaggcg cttctcctcc ctgcacttta tggtggaggt gaaaggcgat      540
ctgactgcca agaaaatggt gctggccctg ctggagctgg cccagcagga ccacggagcc      600
ctggattgct gtgtggtggt gatcctgtcc cacggctgcc aggccagcca cctgcagttc      660
cccggagccg tgtacggcac cgacggctgt cccgtgtccg tggagaagat cgtgaacatc      720
ttcaacggca cctcctgccc ctccctgggc ggcaagccca agctgttctt tatccaggcc      780
tgtggcggcg agcagaagga ccacggcttt gaggtggcca gcacctcccc cgaggacgag      840
agcccaggca gcaaccccga gcccgacgcc acccccttcc aggagggcct gcgcaccttc      900
gaccagctgg acgccatcag cagcctgccc accccccagcg acatcttcgt gagctacagc      960
acctttcccg gcttcgtgag ctggcgcgat cccaagtccg gctcttggta tgtggagacc      1020
ctggacgaca tctttgagca gtgggctcat agcgaggacc tgcagagcct gctgctgcgc      1080
gtggccaatg ccgtgagcgt gaagggcatc tacaagcaga tgccaggctg cttcaacttc      1140
ctgcggaaga agctgttctt caagaccagc gcctcctga                            1179
```

<210> SEQ ID NO 15
<211> LENGTH: 1956
<212> TYPE: DNA
<213> ORGANISM: Artificial Sequence
<220> FEATURE:
<223> OTHER INFORMATION: FKBP12-Casp9-2A-FRB-FRBw nucleotide sequence

<400> SEQUENCE: 15

```
atgctggagg gcgtgcaggt ggagaccatc agcccaggcg acggcagaac cttccccaag      60
agaggccaga cctgcgtggt gcactatacc ggcatgctgg aggacggcaa gaagttcgac      120
agcagccgcg accgcaataa gcccttcaag ttcatgctgg gcaagcagga ggtgatcaga      180 ggctggagg agggcgtggc ccagatgagc gtgggccaga gagccaagct gaccatcagc      240
cccgactacg cctatggcgc caccggccac cccggcatca tcccaccccca cgccaccctg      300 gtgtttgatg tggagctgct gaagctggag tccggaggcg gctccggcgt ggatggcttc      360
ggcgacgtgg gagccctgga gagcctgaga ggcaacgccg atctggccta catcctgagc      420
atggagccct gtggccactg cctgatcatc aacaacgtga acttctgccg ggagagcggc      480
ctgcggaccc ggaccggcag caacatcgac tgcgagaagc tgaggaggcg cttctcctcc      540
ctgcacttta tggtggaggt gaaaggcgat ctgactgcca agaaaatggt gctggccctg      600
ctggagctgg cccagcagga ccacggagcc ctggattgct gtgtggtggt gatcctgtcc      660
cacggctgcc aggccagcca cctgcagttc cccggagccg tgtacggcac cgacggctgt      720
cccgtgtccg tggagaagat cgtgaacatc ttcaacggca cctcctgccc ctccctgggc      780
ggcaagccca agctgttctt tatccaggcc tgtggcggcg agcagaagga ccacggcttt      840
gaggtggcca gcacctcccc cgaggacgag agcccaggca gcaaccccga gcccgacgcc      900
acccccttcc aggagggcct gcgcaccttc gaccagctgg acgccatcag cagcctgccc      960
```

```
acccccagcg acatcttcgt gagctacagc acctttcccg gcttcgtgag ctggcgcgat    1020
cccaagtccg gctcttggta tgtggagacc ctggacgaca tctttgagca gtgggctcat    1080
agcgaggacc tgcagagcct gctgctgcgc gtggccaatg ccgtgagcgt gaagggcatc    1140
tacaagcaga tgccaggctg cttcaacttc ctgcggaaga agctgttctt caagaccagc    1200
gcctcccagt gcaccaatta tgctttgctt aagctggcag gcgatgtgga atcaaacccg    1260
ggtcctgggg tacaggtgga gaccatctct cctggcgacg ggagaacatt tcctaaaagg    1320
ggccaaacat gcgtggttca ctataccggt atgctggagg atggcaaaaa agtagactcc    1380
agccgggata gaaacaaacc ctttaagttc atgctgggta gcaggaagt tatacggggc     1440 tgggaagagg gagtagctca gatgtctgtg gccagaggg ccaagctgac catctcaccg     1500
gactacgcct acggcgctac cggccaccct ggcattatac cacccatgc aactctcgtc     1560 ttcgatgttg agttgctcaa actggaatca ggcggaggcg ggtctggagg aggcggcagc    1620
atgctggagg gcgtgcaggt ggagaccatc agcccaggcg acggcagaac cttccccaag    1680
agaggccaga cctgcgtggt gcactatacc ggcatgctgg aggacggcaa gaagttcgac    1740
agcagccgcg accgcaataa gcccttcaag ttcatgctgg gcaagcagga ggtgatcaga    1800
ggctgggagg agggcgtggc ccagatgagc gtgggccaga gagccaagct gaccatcagc    1860
cccgactacg cctatggcgc caccggccac cccggcatca tcccacccca cgccaccctg    1920
gtgtttgatg tggagctgct gaagctggag tcctga                              1956
```

```
<210> SEQ ID NO 16
<211> LENGTH: 20
<212> TYPE: PRT
<213> ORGANISM: Foot-and-mouth disease virus

<400> SEQUENCE: 16

Arg Ala Glu Gly Arg Gly Ser Leu Leu Thr Cys Gly Asp Val Glu Glu
1               5                   10                  15

Asn Pro Gly Pro
            20

<210> SEQ ID NO 17
<211> LENGTH: 20
<212> TYPE: PRT
<213> ORGANISM: Foot-and-mouth disease virus

<400> SEQUENCE: 17

Gln Cys Thr Asn Tyr Ala Leu Leu Lys Leu Ala Gly Asp Val Glu Ser
1               5                   10                  15

Asn Pro Gly Pro
            20
```